United States Patent
Yoshikawa et al.

(10) Patent No.: US 9,284,432 B2
(45) Date of Patent: Mar. 15, 2016

(54) METHOD FOR DEGRADING A READILY-DEGRADABLE RESIN COMPOSITION

(71) Applicant: TOYO SEIKAN KAISHA, LTD., Tokyo (JP)

(72) Inventors: Seishi Yoshikawa, Yokohama (JP); Tsutaki Katayama, Yokohama (JP); Masahito Kogure, Yokohama (JP)

(73) Assignee: TOYO SEIKAN KAISHA, LTD., Tokyo (JP)

(*) Notice: Subject to any disclaimer, the term of this patent is extended or adjusted under 35 U.S.C. 154(b) by 0 days.

(21) Appl. No.: 14/490,727

(22) Filed: Sep. 19, 2014

(65) Prior Publication Data
US 2015/0010974 A1 Jan. 8, 2015

Related U.S. Application Data

(62) Division of application No. 13/929,083, filed on Jun. 27, 2013, now Pat. No. 8,846,355, which is a division of application No. 13/125,921, filed as application No. PCT/JP2009/068433 on Oct. 27, 2009, now Pat. No. 8,501,445.

(30) Foreign Application Priority Data

Oct. 27, 2008 (JP) ................................ 2008-275738
Nov. 12, 2008 (JP) ................................ 2008-290320
Nov. 12, 2008 (JP) ................................ 2008-290321

(51) Int. Cl.
*C08J 11/10* (2006.01)
*C12P 7/44* (2006.01)
(Continued)

(52) U.S. Cl.
CPC ................ *C08J 11/105* (2013.01); *C12P 7/44* (2013.01); *C12P 7/46* (2013.01); *C12P 7/56* (2013.01); *C12P 7/62* (2013.01); *C08J 2367/04* (2013.01); *Y02W 30/702* (2015.05)

(58) Field of Classification Search
CPC ..................................................... C08J 11/105
See application file for complete search history.

(56) References Cited

U.S. PATENT DOCUMENTS 4,882,178 A 11/1989 Shimamura
6,255,451 B1 * 7/2001 Koch ..................... C08J 11/105
435/18

(Continued)

FOREIGN PATENT DOCUMENTS

JP 11241009 A 9/1999
JP 2001-512504 T 8/2001
(Continued)

OTHER PUBLICATIONS

Isabelle Vroman, et al. "Biodegradable Polymers" Materials 2009, 2, 307-344, www.mdpi.com/journal/materials.
(Continued)

*Primary Examiner* — Rosanne Kosson
(74) *Attorney, Agent, or Firm* — Marshall, Gerstein & Borun LLP

(57) ABSTRACT

A method for degrading a readily degradable resin composition comprising an aliphatic polyester (A) which is biodegradable, and an aliphatic polyester (B') which releases an acid upon hydrolysis and which is biodegradable at a higher degradation rate than that of the aliphatic polyester (A), the method comprising degrading the readily degradable resin composition in an enzyme reaction liquid containing a degradation enzyme, and an acid neutralizing agent incompatible with the enzyme reaction liquid.

5 Claims, 6 Drawing Sheets

(51) Int. Cl.
    C12P 7/46        (2006.01)
    C12P 7/56        (2006.01)
    C12P 7/62        (2006.01)

(56) References Cited

U.S. PATENT DOCUMENTS

| | | |
|---|---|---|
| 2005/0233425 A1 | 10/2005 | Matsumura |
| 2010/0086718 A1 | 4/2010 | Yoshikawa et al. |
| 2011/0201069 A1 | 8/2011 | Yoshikawa et al. |

FOREIGN PATENT DOCUMENTS

| | | |
|---|---|---|
| JP | 2002-293982 A | 10/2002 |
| JP | 2004-058010 A | 2/2004 |
| JP | 2004-269566 A | 9/2004 |
| JP | 2004-290130 A | 10/2004 |
| JP | 2006-104262 A | 4/2006 |
| JP | 2006-124677 A | 5/2006 |
| WO | WO-2004/013217 A1 | 2/2004 |
| WO | WO-2005/045017 A1 | 5/2005 |
| WO | WO-2007/029630 A1 | 3/2007 |
| WO | WO-2008/038648 A1 | 4/2008 |
| WO | WO-2010/050482 A1 | 5/2010 |

OTHER PUBLICATIONS

Yutaka Tokiwa, et al. "Biodegradability of Plastics", International Journal of Molecular Sciences, 2009, 10, 3722-3742, www.mdpi.com/journal/ijms.

European Office Action from Application No. 09823592.2 dated Mar. 2, 2015.

Kobayashi et al., "Lipase-Catalyzed Degradation of Polyesters in Organic Solvents. A New Methodology of Polymer Recycling Using Enzyme as Catalyst," *Biomacromolecules*, 1:3-5 (2000).

Krishna, "Developments and Trends in Enzyme Catalysis in Nonconventional Media," *Biotechnology Advances*, 20:239-266 (2002).

Okajima et al., "Lipase-Catalyzed Transformation of Poly(butylene adipate) and Poly(butylene succinate) into Repolymerizable Cyclic Oligomers," *Biomacromolecules*, 4:1514-1519 (2003).

Perham et al., "Differential Effects of Alcohols on Conformational Switchovers in $\alpha$-Helical and $\beta$-Sheet Protein Models," *Biochemistry*, 45:7740-7749 (2006).

Tomar et al., "Effect of Alkyl Alcohols on Partially Unfolded State of Proteinase K: Differential Stability of $\alpha$-Helix and $\beta$-Sheet Rich Regions of the Enzyme," *Biochimie*, 91:951-960 (2009).

Varma et al., "Enzyme Catalyzed Synthesis of Polyesters," *Prog. Polym. Sci.*, 30:949-981 (2005).

Extended European Search Report for Application No. 09823592.2, dated Jun. 1, 2012.

International Search Report for PCT/JP2009/068433 dated Jan. 12, 2010.

Office Action in Japanese Patent Application No. 2009-246934, mailing date Mar. 25, 2013.

Office Action for Japanese Patent Application No. 2009-258658, mailed on Mar. 25, 2013.

Fukuda et al., Polylactic acid/Biodegradability of inorganic particulate complex and dynamic property, Japan Chemical Society, 81st Springtime Annual Meeting Lecture Proceedings, 81(1):648 (2PC-128) (Mar. 11, 2002).

Office Action, Japanese patent application No. 2009-258659 (mailed on Apr. 1, 2013).

Sivalingam et al., "Solvent Effects on the Lipase Catalyzed Biodegradation of Poly (e-caprolactone) in Solution", Polymer Degradation and Stability 79:413-418, 2003.

\* cited by examiner

DEGRADATION ACTIVITY OF pro K ON POLYLACTIC ACID

DEGRADATION ACTIVITY OF CLE
ON POLYLACTIC ACID

US 9,284,432 B2

METHOD FOR DEGRADING A READILY-DEGRADABLE RESIN COMPOSITION

CROSS-REFERENCE TO RELATED APPLICATIONS

This is a division of U.S. patent application Ser. No. 13/929,083 filed Jun. 27, 2013, which is a division of U.S. patent application Ser. No. 13/125,921 filed Apr. 25, 2011, which is the U.S national phase of PCT/JP2009/068433 filed Oct. 27, 2009 which claims the Convention priority of JP 2008-275738 filed Oct. 27, 2008, JP 2008-290320 filed Nov. 12, 2008, and JP 2008-290321 filed Nov. 12, 2008, the respective entire disclosures of which are incorporated herein by reference

TECHNICAL FIELD

The present invention relates to a method for producing an oligomer and/or a monomer by enzymatically degrading a biodegradable resin, a method for efficiently degrading a readily degradable resin composition, and a degradation liquid.

BACKGROUND ART

Currently, packaging container disposal is at issue. Incineration disposal as in the case of general-purpose resins results in emission of carbon dioxide directly to the environment, and hence is not a good method. Methods of degradation by microorganisms present in the environment, such as landfill disposal, can be expected to reduce addition to the environment. However, such methods take time, and it is difficult to secure land therefor.

Meanwhile, there is proposed a method in which a molded article or the like made of a biodegradable resin is degraded by using an enzyme (see Patent Document 1). In addition, there is proposed a method for depolymerizing polylactic acid to produce oligomers mainly composed of repolymerizable cyclic compounds (see Patent Document 2).

Meanwhile, biodegradable resin compositions such as biodegradable polylactic acid-based resin compositions have been proposed as packaging materials. In general, a packaging container or the like using such a biodegradable resin composition is degraded sequentially from the surface of the container, and complete degradation of the entire container requires a considerable time. Moreover, since the degradation rate of a resin is affected by internal structures of the resin such as the crystallinity of the resin and the molecular orientation therein, there is a problem that the container has some part easy to degrade, but has other part difficult to degrade. In this respect, various biodegradable resin compositions have been developed recently in order to solve these problems. For example, there is reported a readily degradable resin composition with a biodegradability improved by blending an aliphatic polyester which releases an acid upon hydrolysis (Patent Document 3).

Patent Document 1: Published Japanese Translation of PCT International Application No. 2001-512504

Patent Document 2: International Patent Application Publication No. WO2004/013217

Patent Document 3: International Patent Application Publication No. WO2008-038648

DISCLOSURE OF THE INVENTION

Problems to be Solved by the Invention

When, however, a biodegradable resin is degraded by using an enzyme, the enzyme and oligomers and/or a monomer produced by the degradation form aggregates, which eventually makes it difficult to recover the oligomers and/or the monomer. In addition, since the aggregates are not dissolved again, the oligomers and/or the monomer cannot be recovered. Moreover, in the method for depolymerizing polylactic acid to produce oligomers mainly composed of repolymerizable cyclic products, the oligomers cannot be recovered in a high yield because of the low water content in the reaction system. Accordingly, a first object of the present invention is to provide a method for efficiently producing an oligomer and/or a monomer without production of such aggregates, and to provide a method capable of recovering the oligomer and/or the monomer.

In addition, it has been found that when the readily degradable resin composition containing the aliphatic polyester which releases an acid upon hydrolysis as described above is enzymatically degraded in a degradation liquid, the degradation rate decreases with time. Accordingly, a second object of the present invention is to provide a method for more efficiently degrading a readily degradable resin composition containing an aliphatic polyester which releases an acid upon hydrolysis.

Moreover, it has been found that when a readily degradable resin composition containing an aliphatic polyester which releases an acid upon hydrolysis as described above is enzymatically degraded in a degradation liquid, the degrading rate decreases because of the following reasons. Specifically, the acid is released from the readily degradable resin composition with time, and hence the pH of the degradation liquid is lowered, which leads to decrease in activity of the enzymatic degradation. Accordingly, a third object of the present invention is to provide a method for more efficiently degrading a readily degradable resin composition containing an aliphatic polyester which releases an acid upon hydrolysis.

SUMMARY OF THE INVENTION

Means for Solving the Problems

Regarding the above-described first object, the present invention provides a method for producing an oligomer and/or a monomer, comprising degrading a biodegradable resin in a degradation liquid containing a biodegradation enzyme, a buffer agent, an organic solvent, and water, wherein the organic solvent has an SP value of less than 8.5 or more than 11.5, and a percentage content (by volume) of the organic solvent in the degradation liquid is higher than 1% and lower than 15%.

Regarding the above-described second object, the inventors of the present application have found that when the readily degradable resin composition is degraded in a degradation liquid, the acid catalyst is released with time, which results in a low pH of the degradation liquid, and also have found that under such a condition, the activity of the degradation enzyme for the biodegradable resin cannot be exhibited sufficiently. Meanwhile, the inventors have also found that, even in a state where the pH of the degradation liquid is increased, the action of the acidic catalysis of the acid released from the readily degradable resin composition cannot be obtained sufficiently, although the degradation activity of the degradation enzyme is exhibited. In this respect, the inventors have found that, in a case where the readily degradable resin composition containing an aliphatic polyester which releases an acid upon hydrolysis is enzymatically degraded, it is possible to efficiently degrade the readily degradable resin composition by degrading the readily degradable resin composition in an enzyme degradation liquid which is under conditions which make it possible to maintain a pH at which both the degradation action of the acid and the degradation action of the degradation enzyme are simultaneously sufficiently exhibited. These findings have led to completion of the present invention.

Specifically, the present invention provides a method for degrading a readily degradable resin composition comprising an aliphatic polyester (A) which is biodegradable, and an aliphatic polyester (B') which releases an acid upon hydrolysis and which is biodegradable at a higher degradation rate than that of the aliphatic polyester (A), the method comprising: (a) a step of specifying a maximum activity pH value at which a degradation activity value of a hydrolase, when used to degrade a simple polymer of the aliphatic polyester (A) alone in a buffer solution, is maximized; (b) a step of determining an active pH range in which the degradation activity value is not less than 30% of the degradation activity value at the maximum activity pH value; and (c) a step of degrading the readily degradable resin composition in an enzyme reaction liquid containing the hydrolase, and having a pH which is within the active pH range and which is less than 8.0, wherein the pH of the enzyme reaction liquid is maintained within the active pH range and at less than 8.0 in the degradation step.

Regarding the above-described third object, the inventors of the present application have found that when the readily degradable resin composition is degraded in a degradation liquid, the acid catalyst is released with time, which results in a low pH of the degradation liquid, and also have found that under such a condition, the activity of the degradation enzyme for the biodegradable resin cannot be exhibited sufficiently. Meanwhile, the inventors have also found that, even in a state where the pH of the degradation liquid is increased, the action of the acidic catalysis of the acid released from the readily degradable resin composition cannot be obtained sufficiently, although the degradation activity of the degradation enzyme is exhibited. In this respect, the inventors of the present application have found that, by adding, an acid neutralizing agent incompatible with the degradation enzyme to the hydrolase for degrading the readily degradable resin composition, it is possible to maintain a pH at which both the degradation action of the acid and the degradation action of the degradation enzyme can be simultaneously sufficiently exhibited. These findings have led to completion of the present invention.

Specifically, the present invention provides a degradation liquid for degrading a readily degradable resin composition comprising an aliphatic polyester (A) which is biodegradable, and an aliphatic polyester (B') which releases an acid upon hydrolysis and which is biodegradable at a higher degradation rate than that of the aliphatic polyester (A), wherein
the degradation liquid is a liquid mixture containing an enzyme reaction liquid, and an acid neutralizing agent incompatible with the enzyme reaction liquid, and preferably
  1. the acid neutralizing agent is calcium carbonate or chitosan, and/or
  2. a hydrolase is protease, cutinase, cellulase, or lipase.

Moreover, the present invention provides a method for degrading a readily degradable resin composition comprising an aliphatic polyester (A) which is biodegradable, and an aliphatic polyester (B') which releases an acid upon hydrolysis and which is biodegradable at a higher degradation rate than that of the aliphatic polyester (A), the method comprising degrading the readily degradable resin composition in an enzyme reaction liquid containing a degradation enzyme, and an acid neutralizing agent incompatible with the enzyme reaction liquid, and preferably
  1. during the enzyme reaction, the pH of the enzyme reaction liquid is maintained within an active pH range determined by the following steps (a') to (b') and at less than 8.0: and/or
  (a') a step of specifying a maximum activity pH value at which a degradation activity value of the degradation enzyme, when use to degrade a simple polymer of the aliphatic polyester (A) alone in a buffer solution, is maximized;
  (b') a step of determining an active pH range in which the degradation activity value is not less than 30% of the degradation activity value at the maximum activity pH value; and/or
  2. the acid released from the aliphatic polyester (B') is oxalic acid, maleic acid, or glycolic acid; and/or
  3. the readily degradable resin composition is obtained by dispersing a polyoxalate in a polylactic acid-based resin.

DETAILED DESCRIPTION OF THE INVENTION

Effects of the Invention

The method for producing an oligomer and/or a monomer of the present invention makes it possible to efficiently produce an oligomer and/or a monomer at a high degradation percentage of the biodegradable resin, while the production of deposits of aggregates is suppressed during the degradation of the biodegradable resin. In addition, the obtained oligomer can be degraded to the monomer, and the monomer can be repolymerized.

In addition, the degradation method of the present invention makes it possible to improve the degrading rate of the readily degradable resin composition in the degradation liquid because of the degradation effects of both the acid and the degradation enzyme.

BEST MODES FOR CARRYING OUT THE INVENTION

1. Regarding Method for Producing Oligomer and/or Monomer

In a method for producing an oligomer and/or a monomer of the present invention, a biodegradable resin or a formed body containing the biodegradable resin is degraded in a degradation liquid containing a biodegradation enzyme, a buffer agent, an organic solvent, and water.

The oligomer herein refers to a polymeric substance in which monomers are bonded to each other, and examples thereof include a dimer, a trimer, a tetramer, and the like. In addition, the oligomer and/or the monomer may be linear or may have side chains.

The biodegradable resin may be any resin as long as the resin is biodegradable, and examples of the biodegradable resin include chemically synthesized resins, microorganism-based resins, natural product-based resins, and the like. Specific examples thereof include aliphatic polyesters, polyvinyl alcohol (PVA), celluloses, and the like. Examples of the aliphatic polyesters include polylactic acid (PLA) resins, derivatives thereof, polybutylene succinate (PBS) resins, derivatives thereof, polycaprolactone (PCL), polyhydroxybutyrate (PHB), derivatives thereof, polyethylene adipate (PEA), polyglycolic acid (PGA), polytetramethylene adipate, condensation products of a diol and a dicarboxylic acid, and the like. Examples of the celluloses include methyl cellulose, ethyl cellulose, acetyl cellulose, and the like. Moreover, the biodegradable resin may be a modified product or a copolymer of the above-described biodegradable resins, and also may be a mixture of the above-described biodegradable resins, or a mixture of the above-described biodegradable resin with a general-purpose chemical resin, or an additive. Here, examples of the additive include a plasticizer, a heat stabilizer, a light stabilizer, an antioxidant, an ultraviolet absorber, a fire retardant, a coloring agent, a pigment, a filler, an inorganic bulking agent, a mold release agent, an antistatic agent, a flavor and/or fragrance, a lubricant, a foaming agent, an antibacterial/antifungal agent, a nucleating agent, and the like. Examples of a polymer blended with the biodegradable resin include celluloses, chitin, glycogen, chitosan, polyamino acids, starch, and the like.

Preferably, the biodegradable resin contains a degradation accelerator. Those skilled in the art can select as appropriate an acid capable of promoting the degradation of the biodegradable resin, and can use the acid for the degradation accelerator. For example, an acid can be used which releases, upon hydrolysis, an acid showing a pH of 4 or less, for example, an acid showing a pH of 3 or less, an acid showing a pH of 2 or less, for example, an acid showing a pH of 1.5 or less, a pH of 1.3 or less, or a pH of 1.0 or less when dissolved in water at a concentration of 0.005 g/ml. Specific examples of the acid include oxalic acid (pH 1.6), and maleic acid and glycolic acid (pH 2.5). Examples of such a degradation accelerator include polyethylene oxalate, poly (neopentyl) oxalate (PNOx), polyethylene maleate, polyglycolic acid, and the like. Preferred degradation accelerators are polyethylene oxalate and polyglycolic acid. These degradation accelerators may be used as a copolymer, alone, or in combination of two or more kinds.

Examples of other components forming the degradation accelerator or the copolymer include polyvalent alcohols such as ethylene glycol, propylene glycol, butanediol, octanediol, dodecanediol, neopentyl glycol, glycerin, pentaerythritol, sorbitan, bisphenol A, and polyethylene glycol; dicarboxylic acids such as succinic acid, adipic acid, sebacic acid, glutaric acid, decanedicarboxylic acid, cyclohexanedicarboxylic acid, terephthalic acid, isophthalic acid, and anthracene dicarboxylic acid; hydroxy carboxylic acids such as L-lactic acid, D-lactic acid, hydroxypropionic acid, hydroxybutyric acid, hydroxyvaleric acid, hydroxycaproic acid, mandelic acid, and hydroxybenzoic acid; lactones such as glycolide, caprolactone, butyrolactone, valerolactone, propiolactone, and undecalactone; and the like.

In the present description, a polyoxalate means a polymer which may be a homopolymer, a copolymer, or a polymer blend in which oxalic acid is polymerized as at least one monomer.

The content of the degradation accelerator in the biodegradable resin is preferably 1 to 30% by weight, and more preferably 2 to 20% by weight in consideration of mechanical properties and processability.

The biodegradable resin is preferably a polylactic acid resin. The polylactic acid resin is not particularly limited, as long as the polylactic acid resin is a polyester resin obtainable by polymerizing lactic acid. The polylactic acid resin may be a homopolymer, a copolymer, a polymer blend, or the like of polylactic acid.

Examples of components forming the polylactic acid and the copolymer include polyvalent alcohols such as ethylene glycol, propylene glycol, butanediol, octanediol, dodecanediol, neopentyl glycol, glycerin, pentaerythritol, sorbitan, bisphenol A, and polyethylene glycol; dicarboxylic acids such as succinic acid, adipic acid, sebacic acid, glutaric acid, decanedicarboxylic acid, cyclohexanedicarboxylic acid, terephthalic acid, isophthalic acid, and anthracene dicarboxylic acid; hydroxycarboxylic acids such as glycolic acid, L-lactic acid, D-lactic acid, hydroxypropionic acid, hydroxybutyric acid, hydroxyvaleric acid, hydroxycaproic acid, mandelic acid, and hydroxybenzoic acid; lactones such as glycolide, caprolactone, butyrolactone, valerolactone, propiolactone, and undecalactone; and the like.

Examples of the polymer blended include celluloses, chitin, glycogen, chitosan, polyamino acids, starch, and the like. Note that, when polylactic acid is used, the lactic acid used for the polymerization may be any one of the L-isomer and the D-isomer, or a mixture of the L-isomer and the D-isomer.

The biodegradable resin is preferably a readily degradable resin composition including an aliphatic polyester (A) which is biodegradable, and an aliphatic polyester (B') which releases an acid upon hydrolysis, and which is biodegradable at a higher degradation rate than that of the aliphatic polyester (A)

The formed body of the biodegradable resin may be any formed body, as long as the formed body is formed by a known forming method. Examples of the known forming method include injection molding, extrusion molding, sheet forming, and the like. The layer structure of the obtained formed body is not limited to a single layer structure, and accordingly may be a multilayer structure.

The biodegradation enzyme contained in the degradation liquid is not particularly limited, as long as the biodegradation enzyme is a degradation enzyme which acts on the biodegradable polymer. Moreover, the enzyme may be immobilized, but does not necessarily have to be immobilized. Examples of the enzyme include lipase, protease, cutinase, and the like. Alternatively, microorganisms may be contained in the degradation liquid, where an extracellular enzyme thereof is used. Culture medium components and nutrients required by the microorganisms may be added to the degradation liquid. Those skilled in the art can determine as appropriate the amount of the biodegradation enzyme, and can determine the amount, for example, on the basis of an activity unit specific to the enzyme to be used so as to match the biodegradable resin to be degraded.

Examples of the buffer agent contained in the degradation liquid include glycine-hydrochloride buffer solutions, phosphate buffer solutions, tris-hydrochloride buffer solutions, acetate buffer solutions, citrate buffer solutions, citrate-phosphate buffer solutions, borate buffer solutions, tartrate buffer solutions, glycine-sodium hydroxide buffer solutions, and the like. Alternatively, a solid neutralization agent may also be used as the buffer agent, and examples thereof include calcium carbonate, chitosan, deprotonated ion-exchange resins, and the like. Those skilled in the art can determine as appropriate the amount of the buffer agent, and, for example, a buffer solution having a salt concentration of 10 to 100 mM can be used.

The SP value (Hildebrand solubility parameter) of the organic solvent contained in the degradation liquid needs to be less than 8.5 or more than 11.5. Examples of such an organic solvent include hexane (having a SP value of 7.3), cyclohexane (8.2), dimethylsulfoxide (14.4), acetonitrile (11.7), ethanol (12.7), methanol (14.4), and the like. The organic solvent preferably has a SP value of not more than 8.5 or not less than 11.6. More preferably, the SP value is not more than 8 or not less than 12. Further preferably, the SP value is not more than 7.5 or not less than 12.5. When an organic solvent having an SP value within any one of the above-described ranges is used, the degradation percentage of the biodegradable resin is high, and the formation of the aggregates can be suppressed. The organic solvent is preferably ethanol.

The percentage content (by volume) of the organic solvent in the degradation liquid is higher than 1% and lower than 15%. Preferably, the percentage content of the organic solvent is 1.5% to 12%. More preferably, the percentage content of the organic solvent is 2% to 10%. Further preferably, the percentage content of the organic solvent is 4% to 10%. If the percentage content (by volume) of the organic solvent is not higher than 1%, deposits of aggregates are formed in the degradation liquid, which results in reduction in recovery percentage of the oligomer or the monomer. Meanwhile a percentage content of not lower than 15% is not preferable because the degradation percentage of the biodegradable resin decreases.

The percentage content (by volume) of water in the degradation liquid is not lower than 50%. Preferably, the percentage content may be 80 to 99%.

The temperature for the degradation of the biodegradable resin in the degradation liquid may be any, as long as the enzyme exhibits a degradation activity at the temperature. More preferably, the temperature is 0° C. to 100° C. Further preferably the temperature is 20° C. to 70° C. In addition, when the biodegradable resin contains the degradation accelerator, the temperature can be set in further consideration of temperature conditions under which the action of the degradation accelerator is exhibited. In such a case, for example, a standard may be represented as follows: (a temperature which is 5° C. lower than the glass transition temperature of the degradation accelerator)<the degradation temperature<the upper temperature limit of the enzyme activity. For example, when polyethylene oxalate is used as the degradation accelerator, the degradation can be promoted, for example, under a temperature condition of 37° C. Meanwhile, when polyglycolic acid is used as the degradation accelerator, the degradation can be promoted, for example, at 45° C. In addition, the time for degradation of a biodegradable resin (2 cm×2 cm, thickness: 100 µm) in the degradation liquid is preferably 1 day to 10 days, and more preferably 1 day to 7 days. Further preferably, the time is within 4 days. In addition, the stirring conditions of the degradation liquid are not particularly limited, as long as the degradation liquid is stirred uniformly.

2. Regarding Method for Degrading Readily Degradable Resin Composition and Degradation Liquid Therefor In the present invention, the readily degradable resin composition includes an aliphatic polyester (A) which is biodegradable, and an aliphatic polyester (B') which releases an acid upon hydrolysis, and which is biodegradable at a higher degradation rate than that of the aliphatic polyester (A). Examples of the readily degradable resin composition include readily degradable resin compositions described in International Patent Application Publication No. WO2008-038648, and the like.

Examples of the aliphatic polyester (A) which is biodegradable include a polylactic acid resin; polybutylene succinate; polycaprolactone; polyhydroxybutyrate; a polybutylene succinate/adipate copolymer; a copolymer of any of the above-described aliphatic polyesters; a copolymer of any one of the above-described aliphatic polyesters with an aromatic polyester such as polyethylene terephthalate, polyethylene naphthalate, or polybutylene terephthalate. These polyesters may be used alone or in combination of two or more kinds thereof.

Examples of components forming the copolymer of the aliphatic polyester (A) include polyvalent alcohols such as ethylene glycol, propylene glycol, butanediol, octanediol, dodecanediol, neopentyl glycol, glycerin, pentaerythritol, sorbitan, bisphenol A, and polyethylene glycol; dicarboxylic acids such as succinic acid, adipic acid, sebacic acid, glutaric acid, decanedicarboxylic acid, cyclohexanedicarboxylic acid, terephthalic acid, isophthalic acid, and anthracene dicarboxylic acid; hydroxycarboxylic acids such as glycolic acid, L-lactic acid, D-lactic acid, hydroxypropionic acid, hydroxybutyric acid, hydroxyvaleric acid, hydroxycaproic acid, mandelic acid, and hydroxybenzoic acid; lactones such as glycolide, caprolactone, butyrolactone, valerolactone, propiolactone, and undecalactone; and the like.

Examples of the polymer blended include celluloses, chitin, glycogen, chitosan, polyamino acids, starch, and the like. Note that, when polylactic acid is used, the lactic acid used for the polymerization may be any of the L-isomer and the D-isomer, or a mixture of the L-isomer and the D-isomer.

Preferred examples of the aliphatic polyester (A) which is biodegradable include polylactic acid-based resins, polybutylene succinate, and the like.

The molecular weight of the aliphatic polyester (A) which is biodegradable is not particularly limited, and the weight average molecular weight thereof is preferably in a range from 5,000 to 1,000,000, and more preferably in a range from 10,000 to 500,000 in consideration of mechanical properties and processability during the production of a container or the like from the readily degradable resin composition containing the aliphatic polyester (A).

The aliphatic polyester (B') releases an acid upon hydrolysis, and is biodegradable at a higher degradation rate than that of the aliphatic polyester (A). Here, in the present description, "being biodegradable at a higher degradation rate" refers to the fact that, when a simple polymer alone is enzymatically degraded in an aqueous solution, the amount of degradation products eluted per day (degradation rate) is larger (higher) than that of the aliphatic polyester (A), and preferably refers to the fact that the amount of the degradation products (degradation rate) of the single polymer is twice or more as large (high) as that of the aliphatic polyester (A). In the present description, the aliphatic polyester (B') which is biodegradable at a higher degradation rate than that of the aliphatic polyester (A) is referred to as a "readily degradable aliphatic polyester (B')" for the sake of convenience.

The acid to be released is not particularly limited, as long as the acid satisfies the above-described conditions. For example, an acid can be used which releases, upon hydrolysis, an acid showing a pH of 4 or less, for example, an acid showing a pH of 3 or less, an acid showing a pH of 2 or less, for example, an acid showing a pH of 1.5 or less, a pH of 1.3 or less, or a pH of 1.0 or less when dissolved in water at a concentration of 0.005 g/ml. Specific examples thereof include oxalic acid (pH 1.6), maleic acid, maleic anhydride, glycolic acid (pH 2.5), and the like. Among these, oxalic acid, maleic acid, and glycolic acid are preferable. By use of such an aliphatic polyester (B'), the aliphatic polyester (A) is degraded rapidly. This is presumably because, when water enters and elutes the aliphatic polyester (B'), the eluted acid component hydrolyzes the aliphatic polyester (A) such as polylactic acid, causing a large number of cracks inside the aliphatic polyester (A), which in turn increases the surface area on which an enzyme acts. Not only the aliphatic polyester (B') releases the acid upon hydrolysis to leave cracks formed in the aliphatic polyester (A), but also the aliphatic polyester (B') itself is eluted to leave pores formed inside the aliphatic polyester (A).

As a result, a larger number of sites on which the enzyme acts can be formed inside the aliphatic polyester (A), which can further increase the degradation rate.

Examples of the readily degradable aliphatic polyester (B') include polyethylene oxalate, poly(neopentyl) oxalate ($PNO_x$), polyethylene maleate, polyglycolic acid, and the like. These may be used as a copolymer, alone, or in combination of two or more kinds.

Examples of components forming the copolymer include polyvalent alcohols such as ethylene glycol, propylene glycol, butanediol, octanediol, dodecanediol, neopentyl glycol, glycerin, pentaerythritol, sorbitan, bisphenol A, and polyethylene glycol; dicarboxylic acids such as succinic acid, adipic acid, sebacic acid, glutaric acid, decanedicarboxylic acid, cyclohexanedicarboxylic acid, terephthalic acid, isophthalic acid, and anthracene dicarboxylic acid; hydroxycarboxylic acids such as glycolic acid, L-lactic acid, D-lactic acid, hydroxypropionic acid, hydroxybutyric acid, hydroxyvaleric acid, hydroxycaproic acid, mandelic acid, and hydroxybenzoic acid; lactones such as glycolide, caprolactone, butyrolactone, valerolactone, propiolactone, and undecalactone; and the like. In the present description, a polyoxalate means a polymer which may be a homopolymer, a copolymer, or a polymer blend in which oxalic acid is polymerized as at least one monomer.

Among these, preferred degradation accelerators are polyoxalate and polyglycolic acid.

The readily degradable aliphatic polyester (B') is preferably dispersed in the aliphatic polyester (A). The enzyme can enter voids from which the readily degradable aliphatic polyester (B') is eluted by degradation in water, and the enzyme in the voids acts thereon. Thus, the readily degradable resin composition is degraded not only from the surface thereof, but also from the inside thereof. For this reason, the degradation rate is increased. Examples of such a readily degradable resin composition include readily degradable resin compositions each obtained by dispersing a polyoxalate or polyglycolic acid in a polylactic acid-based resin.

Here, in order to attain a good degradation rate, the readily degradable aliphatic polyester (B') is preferably present in the aliphatic polyester (A) in a uniformly and finely dispersed manner. One or more monomer components of the aliphatic polyester (A) may be polymerized in the readily degradable aliphatic polyester (B'), in order to improve the dispersibility of the readily degradable aliphatic polyester (B') in the aliphatic polyester (A).

Furthermore, the readily degradable aliphatic polyester (B') is preferably highly polarized, i.e., preferably has a high affinity for water. Such a readily degradable aliphatic polyester (B') has an increased hydrolysis rate. Thus, a large number of pores are formed rapidly inside the aliphatic polyester (A), which increase the area on which the enzyme acts. As a result, the degradation rate of the aliphatic polyester (A) is also increased. The polarity can be indicated by a SP value (solubility parameter) calculated by the Fedors method (Polym. Eng. Sci., 14, 147-154 (1974)), or the like. The SP value may be, in an example case, 22.0 or more, 23.0 or more, or 24.0 or more, and is preferably 25.0 or more.

The content of the readily degradable aliphatic polyester (B') in the readily degradable resin composition degraded by the method of the present invention is preferably 1 to 30% by weight, and more preferably 2 to 20% by weight in consideration of mechanical properties and processability during the production of a container and the like from the readily degradable resin composition containing the readily degradable aliphatic polyester (B').

The readily degradable resin composition degraded by the method of the present invention can be produced by uniformly mixing the biodegradable aliphatic polyester (A) and the readily degradable aliphatic polyester (B') by an ordinary method. For example, the biodegradable aliphatic polyester (A) and the readily degradable aliphatic polyester (B') are simultaneously fed to a single- or twin-screw extruder-kneader to thereby be melt-mixed, and thereafter are palletized. Thus, the readily degradable resin composition of the present invention can be produced. The melt-extrusion temperature is generally 100 to 250° C.; however, those skilled in the art can set any melt-extrusion temperature appropriately, in consideration of the glass transition temperatures, the melting points, and the mixing ratio of the biodegradable aliphatic polyester (A) and the readily degradable aliphatic polyester (B') to be used.

The readily degradable resin composition degraded by the method of the present invention may be blended with known additives such as a plasticizer, a heat stabilizer, a light stabilizer, an antioxidant, an ultraviolet absorber, a fire retardant, a coloring agent, a pigment, a filler, a bulking agent, a mold release agent, an antistatic agent, a flavor and/or fragrance, a lubricant, a foaming agent, an antibacterial/antifungal agent, and a nucleating agent, if necessary. The readily degradable resin composition degraded by the method of the present invention may also be blended with a resin other than the biodegradable aliphatic polyester (A) and than the readily degradable aliphatic polyester (B') within a range not impairing effects of the present invention. For example, the readily degradable resin composition can be blended with water soluble resins such as polyethylene glycol and polyvinyl alcohol, as well as polyethylene, polypropylene, an ethylene-propylene copolymer, an acid modified polyolefin, an ethylene-methacrylic acid copolymer, an ethylene-vinyl acetate copolymer, an ionomer resin, polyethylene terephthalate, polybutylene terephthalate, polyvinyl acetate, polyvinyl chloride, polystyrene, a polyester rubber, a polyamide rubber, a styrene-butadiene-styrene copolymer, or the like. The readily degradable resin composition may be blended with a copolymer of the biodegradable aliphatic polyester (A) and the readily degradable aliphatic polyester (B') in order to improve the dispersibility of the readily degradable aliphatic polyester (B').

A forming method known per se can be used to produce a container using the readily degradable resin composition to be degraded by the method of the present invention.

For example, a multilayer film, a multilayer sheet, a multilayer parison, a multilayer pipe, and the like can be molded by extrusion molding using multiple extruders, the number of the multiple extruders being equivalent to the number of kinds of the resins and using a multiple die for multilayer. Meanwhile, a multilayer preform for bottle formation can be produced by co-injection molding such as a simultaneous injection method or a sequential injection method using multiple injection molding machines, the number of the injection molding machines being equivalent to the number of kinds of the resins. By further processing such a multilayer film, parison or preform, the container using the readily degradable resin composition to be used in the method of the present invention can be obtained.

A packaging material such as a film can be used for a pouch in various forms or for a top member of a tray or a cup. Examples of the pouch includes three- or four-side sealed flat pouches, pouches with a gusset, standing pouches, pillow packaging bags, and the like. These pouches and bags can be produced by a known pouch or bag forming method. Meanwhile, a packaging container in a cup shape, a tray shape, or the like can be obtained by subjecting the film or the sheet to means such as vacuum molding, pressure molding, bulge forming or plug-assist molding.

An extrusion coating method or a sandwich lamination can be used to produce a multilayer film or a multilayer sheet. Meanwhile, a single-layer or multilayer film formed in advance can be laminated by dry lamination to produce a multilayer film or a multilayer sheet. Examples of the production method include a method in which a transparent biodegradable deposition film is dry laminated on a double layered co-extrusion film formed of the readily degradable resin composition/a polylactic acid (sealant) layer; a method in which two layers of the readily degradable resin composition/polylactic acid (sealant) are extrusion coated onto a double layered film of polylactic acid/polyglycolic acid dry-laminated on each other with an anchoring agent interposed therebetween; and the like. However, the production method is not limited to these.

In addition, a bottle or a tube can be easily molded by pinching off a parison, a pipe, or a preform with a pair of split dies and then by blowing a fluid into the pinched-off parison, pipe or preform. In addition, an oriented blow-molded bottle and the like can be obtained as follows. Specifically, a pipe or a preform is cooled, thereafter, heated to an orientation temperature, and then oriented in the axial direction, while blow-oriented in the circumferential direction by a fluid pressure.

The hydrolase used in the present invention is not particularly limited, as long as the hydrolase generally degrades biodegradable resins. Those skilled in the art can use any degradation enzyme. Examples of such an enzyme include protease, cellulase, cutinase, lipase, and the like. For example, it is possible to use protease K manufactured by Wako Pure Chemical Industries, Ltd. or lipase CS2 of National Research Institute of Brewing. Those skilled in the art can determine as appropriate the amount of the hydrolase, and may determine the amount, for example, on the basis of active unit specific to the enzyme to be used so as to match the readily degradable resin to be degraded.

The buffer solution used in the present invention is not particularly limited, as long as the buffer solution is a buffer solution generally used to stabilize pH. Examples of such a buffer solution include glycine-hydrochloride buffer solutions, phosphate buffer solutions, tris-hydrochloride buffer solutions, acetate buffer solutions, citrate buffer solutions, citrate-phosphate buffer solutions, borate buffer solutions, tartrate buffer solutions, glycine-sodium hydroxide buffer solutions, and the like. Alternatively, a solid neutralizing agent may also be used for the buffer solution, and examples thereof include calcium carbonate, chitosan, deprotonated ion-exchange resins, and the like. Those skilled in the art can determine as appropriate the concentration of the buffer solution, and, for example, a buffer solution having a salt concentration of 10 to 100 mM can be used.

In step (a) of the present invention, a maximum activity pH value is specified at which a degradation activity of a hydrolase in a case where a simple polymer of the aliphatic polyester (A) alone is degraded in the buffer solution by the hydrolase is maximized. The simple polymer of the aliphatic polyester (A) is made of the aliphatic polyester (A) alone, which is one of the components of the above-described readily degradable resin composition. One having the same shape as the readily degradable resin composition to be degraded is preferably used. Conditions such as the amount of the degradation liquid and the temperature thereof can be set as appropriate by those skilled in the art, and are preferably set to the same as those in step (c) to be described later.

In this step, multiple experiments on the degradation of the simple polymer of the aliphatic polyester (A) alone are conducted by using buffer solutions of different pH values to specify the maximum activity pH value at which the degradation activity value of the hydrolase which degrades the simple polymer of the aliphatic polyester (A) alone is maximized. The degradation activity value can be determined, for example, based on a degradation amount of the aliphatic polyester (A) in a certain period of time, and may be determined in modified manners depending on the mode of the degradation of the readily degradable resin composition. Regarding the number of pH values set for the buffer solutions and the intervals of the pH values, those skilled in the art can determine values necessary for specifying an optimal pH for the degradation. The pHs of the buffer solutions of various pHs used in the step do not necessarily have to cover the entire pH region, and the intervals thereof do not necessarily have to be the same. Those skilled in the art can set the values based on a peak of the degradation activity value which is roughly estimated for an ordinary case so that the values can have an appropriate distribution.

In step (b) of the present invention, a pH range in which the degradation activity value is not less than 30% of the degradation activity value at the maximum activity pH value is determined. Generally, an enzyme activity has an optimum pH, which varies depending on the kind of the enzyme, reaction conditions, and the like, and the activity can be represented by a mountain-like shape with the optimum pH being a peak. Accordingly, it is possible to easily determine an active pH range in which an activity not less than 30% of the degradation activity at the maximum activity pH value specified in step (a) is exhibited, by forming a graph showing change in activity of the degradation enzyme with change in pH in step (a). Note that, in the present invention, it is not necessary to set a limit of the degradation activity value in a strict manner, but those skilled in the art can determine a value, with a certain width, necessary for degrading the readily degradable resin composition to a desired extent in accordance with the absolute value of the degradation activity value or the distribution of the degradation activity.

In step (c) of the present invention, the readily degradable resin composition (i.e., the resin composition containing both the aliphatic polyester (A) and the aliphatic polyester (B')) is degraded in an enzyme reaction liquid containing the hydrolase and having a pH which is within the active pH range, and which is less than 8.0. Here, during the degradation step, the pH of the enzyme reaction liquid is maintained in a range which is within the active pH range and which is less than 8.0. By setting the pH within the active pH range, the action of the hydrolase can be obtained sufficiently, and simultaneously by employing a pH less than 8.0, the degradation action of the acid showing a pH of 2.0 or less released upon hydrolysis from the aliphatic polyester (B') released upon hydrolysis can be obtained sufficiently. Accordingly, the degradation actions of both the acid and the degradation enzyme can improve the degrading rate of the readily degradable resin composition.

In this step, the pH value of the enzyme reaction liquid is maintained under the above-described pH conditions. Specifically, not only at the beginning of the reaction immediately after the readily degradable resin composition is introduced into the enzyme reaction liquid, but also throughout this step, i.e., for a period of time necessary for degrading the readily degradable resin composition to a desired extent, the pH is within the pH range. However, deviation of the pH from the above-described pH range for a short period of time is acceptable, and the pH value only needs to be controlled within the range to such an extent that a period of time necessary for the degradation of the readily degradable resin composition is secured.

A method for maintaining the pH in a range which is within the active pH range and which is less than 8.0 is not particularly limited, and those skilled in the art can employ any method. For maintaining the pH, for example, the enzyme degradation liquid may be replaced after a predetermined period of time, for example, two days or three days, has elapsed; the concentration of the buffer solution may be adjusted within a range not affecting the activity of the degradation enzyme; or a neutralizing agent such as calcium carbonate may be added to the enzyme degradation liquid.

Additionally, according to the degradation method of the present invention using an acid neutralizing agent incompatible with an enzyme reaction liquid, a readily degradable resin composition is degraded in an enzyme reaction liquid containing a degradation enzyme, and an acid neutralizing agent incompatible with the enzyme reaction liquid, the readily degradable resin composition including an aliphatic polyester (A) which is biodegradable, and an aliphatic polyester (B') which releases an acid upon hydrolysis and which is biodegradable at a higher degradation rate than that of the aliphatic polyester (A). Thus, the degradation rate of the readily degradable resin composition can be improved, and the readily degradable resin composition can be degraded efficiently in a short period of time.

Although the exact reason for this is not clarified, the following are possible. The surface of the readily degradable resin composition is degraded through enzymatic degradation, and the inside thereof is degraded by the acid such as oxalic acid released upon hydrolysis. Then, the acid such as oxalic acid or lactic acid eluted to the outside from the readily degradable resin composition is neutralized with the acid neutralizing agent, and moreover the acid neutralizing agent does not enter the inside of the readily degradable resin composition, and thus does not inhibit the degradation by the acid. As a result, the initial degradation rate is extremely high.

The degradation method of the present invention using an acid neutralizing agent incompatible with an enzyme reaction liquid is characterized in that the readily degradable resin composition is degraded in an enzyme reaction liquid containing a degradation enzyme, and an acid neutralizing agent incompatible with the enzyme reaction liquid.

The degradation enzyme used in the degradation method of the present invention in which the acid neutralizing agent incompatible with the enzyme reaction liquid is used is not particularly limited, as long as the degradation enzyme generally degrades biodegradable resins. Those skilled in the art can use any degradation enzyme. Examples of such an enzyme include protease, cellulase, cutinase, lipase, and the like. For example, it is possible to use protease K manufactured by Wako Pure Chemical Industries, Ltd. or lipase CS2 of National Research Institute of Brewing. The amount of the enzyme added to the enzyme reaction liquid can be determined as appropriate by those skilled in the art on the basis of the kind of the enzyme, the amount of the film, and the like, and is not particularly limited. For example, when a powder of Tritirachium album-derived Proteinase K (manufactured by Wako Pure Chemical Industries, Ltd.) is used, the powder can be used in an amount of 1 to 10 µg, preferably 5 to 8 µg per milligram of the biodegradable resin to be degraded.

In the present invention, the meaning of the acid neutralizing agent incompatible with the enzyme reaction liquid include general acid neutralizing agents other than liquid neutralizing agents, and than solid or semi-solid neutralizing agents and the like which easily and completely dissolve in the enzyme reaction liquid under conditions generally employed for enzyme reaction in a liquid, and is not particularly limited. Such neutralizing agents are known to those skilled in the art, and examples thereof include calcium carbonate, chitosan, cation exchange resins, and the like. Among these, calcium carbonate or chitosan is preferable in the present invention.

The solubility of the acid neutralizing agent used in the present invention varies depending on the composition, the temperature, and the like of the enzyme reaction liquid. However, the kind of the acid neutralizing agent is not particularly limited, as long as the acid neutralizing agent can stably maintain the pH within the enzyme activity pH range under the test conditions. In addition, the amount of the neutralizing agent can be determined as appropriate by those skilled in the art, and is not particularly limited. The amount can be, for example, 0.2 to 2 times, preferably 0.5 to 1.5 times the weight of a film of the biodegradable resin to be degraded.

In addition, as described above, it is presumed that the degradation rate of the readily degradable resin used in the present invention is increased because, when water enters and elutes the aliphatic polyester (B'), the eluted acid component hydrolyzes the aliphatic polyester (A) such as polylactic acid, causing a large number of cracks inside the aliphatic polyester (A), which in turn increase the surface area on which an enzyme acts. For this reason, to prevent neutralization of the acid which plays a role in the degradation inside the readily degradable resin, it is preferable to employ conditions under which the neutralizing agent does not enter the inside of cracks. By employing such conditions, the neutralizing agent does not inhibit the action of the acid which degrades the readily degradable resin inside the readily degradable resin, whereas, only after the aliphatic polyester (B') of the readily degradable resin is eluted into the enzyme reaction liquid, the neutralizing agent neutralizes the acid and forms a salt to thereby prevent the decrease in pH of the enzyme reaction liquid so that the activity of the degradation enzyme can be exhibited to the maximum extent possible. The above-described conditions can be achieved by adjusting the particle diameter of the neutralizing agent to a certain value or larger in consideration of the relationship with the size of the cracks. For example, when the pores formed as a result of degradation of the aliphatic polyester (B') are approximately 10 µm in size, the particle diameter of the neutralizing agent is preferably set to 10 µm or larger.

In the degradation method of the present invention using an acid neutralizing agent incompatible with an enzyme reaction liquid, preferably, the pH of the enzyme reaction liquid is maintained during the enzyme reaction in a range which is within an active pH range determined by the following steps (a') to (b'), and which is less than 8.0:

(a') a step of specifying a maximum activity pH value at which a degradation activity value of the degradation enzyme in a case where a simple polymer of the aliphatic polyester (A) alone is degraded in a buffer solution by the hydrolase is maximized; and (b') a step of determining an active pH range in which the degradation activity value is not less than 30% of the degradation activity value at the maximum activity pH value.

In step (a), a maximum activity pH value is specified at which a degradation activity value of a hydrolase in a case where a simple polymer of the aliphatic polyester (A) alone is degraded in a buffer solution by the hydrolase is maximized. The simple polymer of the aliphatic polyester (A) is made of the aliphatic polyester (A) alone, which is one of the components of the above-described readily degradable resin composition. One having the same shape as the readily degradable resin composition to be degraded is preferably used. Conditions such as the amount of the degradation liquid and the temperature thereof can be set as appropriate by those skilled in the art, and are preferably set to the same as those in degrading the readily degradable resin composition.

The buffer solution used in the present invention is not particularly limited, as long as the buffer solution is a buffer solution generally used to stabilize pH. Examples of such a buffer solution include glycine-hydrochloride buffer solutions, phosphate buffer solutions, tris-hydrochloride buffer solutions, acetate buffer solutions, citrate buffer solutions, citrate-phosphate buffer solutions, borate buffer solutions, tartrate buffer solutions, glycine-sodium hydroxide buffer solutions, and the like.

In this step, multiple experiments on the degradation of the simple polymer of the aliphatic polyester (A) alone are conducted by using buffer solutions of different pH values to specify the maximum activity pH value at which the degradation activity value of the degradation enzyme which degrades the simple polymer of the aliphatic polyester (A) alone is maximized. The degradation activity value can be determined, for example, based on a degradation amount of the aliphatic polyester (A) in a certain period of time, and may be determined in modified manners depending on the mode of the degradation of the readily degradable resin composition. Regarding the number of pH values set for the buffer solutions and the intervals of the pH values, those skilled in the art can determine values necessary for specifying an optimal pH for the degradation. The pHs of the buffer solutions of various pHs used in this step do not necessarily have to cover the entire pH region, and the intervals thereof do not necessarily have to be the same. Those skilled in the art can set the values based on a peak of the degradation activity value which is roughly estimated for an ordinary case so that the values can have an appropriate distribution.

In step (b'), a pH range in which the degradation activity value is not less than 30% of the degradation activity value at the maximum activity pH value is determined. Generally, an enzyme activity has an optimum pH, which varies depending on the kind of the enzyme, reaction conditions, and the like, and the activity can be represented by a mountain-like shape with the optimum pH being a peak. Accordingly, it is possible to easily determine an active pH range in which an activity not less than 30% of the degradation activity value at the maximum activity pH value specified in step (a') is exhibited, by forming a graph showing change in activity of the degradation enzyme with change in pH in step (a'). Note that, in the present invention, it is not necessary to set a limit of the degradation activity value in a strict manner, but those skilled in the art can determine a value, with a certain width, necessary for degrading the readily degradable resin composition to a desired extent in accordance with the absolute value of the degradation activity value or the distribution of the degradation activity.

In a preferred method of the present invention, by adding the acid neutralizing agent incompatible with the enzyme reaction liquid to the enzyme reaction liquid for degrading the readily degradable resin composition (i.e., the resin composition containing both the aliphatic polyester (A) and the aliphatic polyester (B')), the pH thereof can be controlled within a certain range. Here, by setting the pH within the active pH range determined through the steps (a') to (b'), the action of the hydrolase can be obtained sufficiently, and simultaneously by employing a pH less than 8.0, the degradation action of the acid showing a pH of 2.0 or less released upon hydrolysis from the aliphatic polyester (B') released upon hydrolysis can be obtained sufficiently. Accordingly, the degradation actions of both the acid and the degradation enzyme can improve the degrading rate of the readily degradable resin composition.

In the preferred mode, the pH of the enzyme reaction liquid is maintained under the above-described pH conditions during the enzyme reaction. Specifically, not only at the beginning of the reaction immediately after the readily degradable resin composition is introduced into the enzyme reaction liquid, but also throughout the degradation, i.e., for a period of time necessary for degrading the readily degradable resin composition to a desired extent, the pH is maintained within the above-described pH range. However, deviation of the pH from the above-described pH range for a short period of time is acceptable, and the pH value only needs to be controlled within the range to such an extent that a period of time necessary for the degradation of the readily degradable resin composition is secured.

The temperature for degradation of the readily degradable resin in the degradation liquid may be any, as long as the enzyme and the acid released from the readily degradable aliphatic polyester (B') exhibit their degradation activities at the temperature. More preferably, the temperature is 0° C. to 100° C. Further preferably, the temperature is 20° C. to 70° C. More specifically, a standard for the temperature for the degradation is, for example, represented as follows: (a temperature which is 5° C. lower than the glass transition temperature of the readily degradable aliphatic polyester (B'))<the degradation temperature<the upper temperature limit of the enzyme activity. For example, when polyethylene oxalate is used as the readily degradable aliphatic polyester (B'), the degradation can be promoted, for example, under a temperature condition of 37° C. Meanwhile, when polyglycolic acid is used as the readily degradable aliphatic polyester (B'), the degrading can be promoted, for example, at 45° C.

According to the degradation method of the present invention, the degradation rate of the readily degradable resin composition can be improved by the degradation actions of both the acid and the degradation enzyme in the degradation liquid.

Hereinafter, Examples of the present invention will be described. However, the present invention is not limited thereto.

EXAMPLES

1. Examples A-1 to 12 and Comparative Example A-1 to 17 were conducted as follows.

(Pro K (Proteinase K) Enzyme Solution)

A pro K (proteinase K) enzyme solution was prepared by dissolving 20 mg of a Tritirachium album-derived proteinase K powder in 1 ml of a 0.05 M Tris-HCl buffer solution (pH 8.0) containing 50 w/w % of glycerin.

(CLE Enzyme Solution)

A *Cryptococcus* sp. S-2-derived lipase CS2 (Japanese Patent Application Publication No. 2004-73123: provided by National Research Institute of Brewing) enzyme solution having a lipase activity of 653 U/mL was used. The lipase activity was measured by using para-nitrophenyl laurate as the substrate. Here, 1 U of the lipase activity is defined as the amount of enzyme with which para-nitrophenol is liberated from para-nitrophenyl laurate at 1 μmol/min.

(Measurement of Glass Transition Temperature)

The glass transition temperature (Tg) was measured by using DSC 6220 manufactured by Seiko Instruments Inc. (differential scanning calorimetry). As for the measurement conditions, the measurement was conducted in an nitrogen atmosphere at a rate of temperature rise of 10° C. per minute from 0 to 200° C. The samples used were PEOx and PEOx 20 to be described later, and the amount of each sample was 5 to 10 mg.

(Synthesis of Polyethylene Oxalate (PEOx))

Into a 300-mL separable flask equipped with a mantle heater, a stirrer, a nitrogen inlet, and a condenser, 354 g (3.0 mol) of dimethyl oxalate, 223.5 g (3.6 mol) of ethylene glycol, and 0.30 g of tetrabutyl titanate were introduced. The flask was heated under nitrogen stream from 110° C. until the inside temperature reached 170° C., while methanol was being distilled off. Thus, the reaction was conducted for 9 hours.

At the end, 210 ml of methanol was distilled off. Thereafter, stirring was performed for 1 hour at an inside temperature of 150° C. and at a reduced pressure of 0.1 to 0.5 mmHg. After a 7-hour reaction at an inside temperature of 170° C. to 190° C., the viscosity increased, and the product was taken out. The η inh of the synthesized product was 0.12.

The solution viscosity (η inh) was measured as follows. Specifically, the synthesized polyethylene oxalate that had been vacuum-dried at 120° C. overnight was used. The polyethylene oxalate was immersed in a mixture solvent of m-chlorophenol/1,2,4-trichlorobenzene=4/1 (weight ratio) and dissolved thereinto at 150° C. in approximately 10 minutes to prepare a solution at a concentration of 0.4 g/dl. Thereafter, the solution viscosity was measured at 30° C. by use of an Ubbelohde viscometer (Unit: dl/g).

(Synthesis of Polyoxalate (PEOx 20))

The PEOx 20 was synthesized by the same method as in the above-described synthesis of the PEOx, except that 94.5 g (0.8 mol) of dimethyl oxalate and 38.8 g (0.2 mol) of dimethyl terephthalate were used instead of 354 g (3.0 mol) of dimethyl oxalate.

GPC measurement showed that the weight average molecular weight (Mw) of the PEOx was 20000. The GPC used was HLC-8120 manufactured by Tosoh Corporation, the columns used were two TSK gel Super HM-H columns, and the guard column used was a TSK guard column Super H-H column. The temperature of a column oven was set to 40° C. Chloroform was used as an eluent, and the flow rate thereof was set to 0.5 ml/min. The amount of sample injected was 15 μl. Polystyrene dissolved in chloroform was used as a standard. As for sample preparation, chloroform was used as a solvent with a sample concentration of 5 mg/ml, and the sample was filtered before use.

(Properties of PEOx and PEOx 20)

The monomer, oxalic acid, shows a pH of 1.6 at a concentration of 0.005 g/ml. The PEOx releases, upon hydrolysis, oxalic acid or oxalic acid oligomers in an aqueous solution.

TABLE 1

Monomer Contents in Polyoxalate and Glass Transition Temperature thereof

| | Dimetyl Oxalate (mol) | Terephthalic Acid (mol) | Ethylene Glycol (mol) | Tg (° C.) |
|---|---|---|---|---|
| PEOx | 3 | 0 | 3.6 | 25 |
| PEOx 20 | 0.8 | 0.2 | 1.2 | 45 |

(Fabrication of Biodegradable Resin (Polylactic Acid/PEOx) Film)

Master pellets of polylactic acid (4032D manufactured by NatureWorks LLC)/polyethylene oxalate=95/5 wt % were melt blended at 200° C. by using a twin-screw extruder (ULT Nano 05-20AG manufactured by Technovel Corporation), and then formed into a readily degradable resin composition film having a thickness of 100 μm by using Labo Plastomill (manufactured by Toyo Seiki Seisaku-sho, Ltd.).

(Fabrication of Biodegradable Resin (Polylactic Acid/PEOx 20) Film)

The fabrication was conducted in the same manner, except that the PEOx was replaced with the PEOx 20.

(Fabrication of Biodegradable Resin (PBS) Film)

Polybutylene succinate (PBS) (#1001 manufactured by Showa High Polymer Co., Ltd.) pellets were melted at 200° C. for 5 minutes, and then heated and pressed at a pressure of 50 kgf/cm2 to form a film thereof.

(Degradation Percentage)

For the degradation percentage, the initial weight of the biodegradable resin film was measured, and the weight of the biodegradable resin film after being degraded for one week was measured. Then, the degradation percentage was calculated by using the following formula.

((initial weight of biodegradable resin film−weight of film after degradation)/initial weight of biodegradable resin film)×100=degradation percentage (%)

(Transparency of Degradation Liquid)

The transparency of each degradation liquid in which the film was degraded was visually observed. A transparent degradation liquid was evaluated as ◯, and a degradation liquid in which white turbidity was observed immediately after the degradation was evaluated as x.

(Absorbance Measurement (Turbidity Measurement))

The absorbance of each degradation liquid in which the film was degraded was measured by using a spectrophotometer UV-160A manufactured by Shimadzu Corporation at a wavelength of 660 nm.

(Preparation Method of 60 mmol/l Phosphate Buffer Solution (pH 7))

A 60 mmol/l sodium dihydrogen phosphate aqueous solution and a 60 mM disodium hydrogen phosphate aqueous solution were mixed with each other at a ratio of 1:1, and the pH of the mixture was adjusted to 7 with a 60 mmol/l sodium dihydrogen phosphate aqueous solution.

(Method for Preparing Buffer Solution Containing Organic Solvent)

Hereinbelow, a preparation method of a buffer solution containing 4% of ethanol is described.

Ethanol was added to the above-described 60 mmol/L phosphate buffer solution to obtain an ethanol percentage content (by volume) of 4%, and the pH was adjusted to 7 with 1 mol/l hydrochloric acid. Thus, a buffer solution containing an organic solvent was prepared. The liquid was termed as a 4% ethanol-containing buffer solution.

Example A-1

A degradation liquid was prepared by mixing 10 ml of the 60 mmol/L phosphate buffer solution (pH 7), 12 μl of the CLE enzyme solution, and ethanol in such a manner that the ethanol percentage content in the degradation liquid became 4%. Then the pH of the degradation liquid was adjusted to 7 by adding hydrochloric acid thereto. Into a 25-ml vial, the degradation liquid and the biodegradable resin (polylactic acid/ PEOx) film cut into 2 cm×2 cm (weight: 50 mg) were introduced, and shaken at 37° C. and 100 rpm for 7 days. Note that to avoid a too-much decrease in pH, the 7 days was divided into 2 days, 2 days, and 3 days, between which the degradation liquid was replaced.

Example A-2

Example A-2 was conducted in the same manner as in Example A-1, except that the ethanol percentage content was set to 2%.

Example A-3

Example A-3 was conducted in the same manner as in Example A-1, except that the ethanol percentage content was set to 7%.

Example A-4

Example A-4 was conducted in the same manner as in Example A-1, except that the ethanol percentage content was set to 10%.

Example A-5

Example A-5 was conducted in the same manner as in Example A-1, except that hexane was used instead of ethanol, and that the percentage content of hexane was set to 4%.

Example A-6

Example A-6 was conducted in the same manner as in Example A-1, except that hexane was used instead of ethanol, and that the percentage content of hexane was set to 10%.

Example A-7

Example A-7 was conducted in the same manner as in Example A-1, except that methanol was used instead of ethanol, and that the percentage content of methanol was set to 4%.

Example A-8

Example A-8 was conducted in the same manner as in Example A-1, except that acetonitrile was used instead of ethanol, and that the percentage content of acetonitrile was set to 4%.

Example A-9

Example A-9 was conducted in the same manner as in Example A-1, except that the biodegradable resin (polylactic acid/PEOx) film was replaced with the biodegradable resin (PBS) film.

Example A-10

Example A-10 was conducted in the same manner as in Example A-5, except that the biodegradable resin (polylactic acid/PEOx) film was replaced with the biodegradable resin (PBS) film.

Example A-11

Example A-11 was conducted in the same manner as in Example A-1, except that 12 µl of the pro K enzyme solution was used.

Example A-12

Example A-12 was conducted in the same manner as in Example A-1, except that the biodegradable resin (polylactic acid/PEOx) film was replaced with the biodegradable resin (polylactic acid/PEOx 20) film, and that the degradation temperature was changed to 45° C.

Comparative Example A-1

Comparative Example A-1 was conducted in the same manner as in Example A-1, except that the ethanol percentage content was set to 1%.

Comparative Example A-2

Comparative Example A-2 was conducted in the same manner as in Example A-1, except that the ethanol percentage content was set to 15%.

Comparative Example A-3

Comparative Example A-3 was conducted in the same manner as in Example A-1, except that the ethanol percentage content was set to 20%.

Comparative Example A-4

Comparative Example A-4 was conducted in the same manner as in Example A-1, except that the ethanol percentage content was set to 30%.

Comparative Example A-5

Comparative Example A-5 was conducted in the same manner as in Example A-1, except that toluene was used instead of ethanol, and that the percentage content of toluene was set to 4%.

Comparative Example A-6

Comparative Example A-6 was conducted in the same manner as in Example A-1, except that toluene was used instead of ethanol, and that the percentage content of toluene was set to 50%.

Comparative Example A-7

Comparative Example A-7 was conducted in the same manner as in Example A-1, except that toluene was used instead of ethanol, and that the percentage content of toluene was set to 95%.

Comparative Example A-8

Comparative Example A-8 was conducted in the same manner as in Example A-1, except that chloroform was used instead of ethanol, and that the percentage content of chloroform was set to 4%.

Comparative Example A-9

Comparative Example A-9 was conducted in the same manner as in Example A-1, except that ethyl acetate was used instead of ethanol, and that the percentage content of ethyl acetate was set to 4%.

Comparative Example A-10

Comparative Example A-10 was conducted in the same manner as in Example A-1, except that isopropanol was used instead of ethanol, and that the percentage content of isopropanol was set to 4%.

Comparative Example A-11

Comparative Example A-11 was conducted in the same manner as in Example A-1, except that dioxane was used instead of ethanol, and that the percentage content of dioxane was set to 4%.

Comparative Example A-12

Comparative Example A-12 was conducted in the same manner as in Example A-1, except that hexane was used instead of ethanol, and that the percentage content of hexane was set to 1%.

Comparative Example A-13

Comparative Example A-13 was conducted in the same manner as in Example A-1, except that methanol was used instead of ethanol, and that the percentage content of methanol was set to 1%.

Comparative Example A-14

Comparative Example A-14 was conducted in the same manner as in Example A-1, except that no ethanol was added.

Comparative Example A-15

Comparative Example A-15 was conducted in the same manner as in Comparative Example A-14, except that the biodegradable resin (polylactic acid/PEOx) film was replaced with the biodegradable resin (PBS) film.

Comparative Example A-16

Comparative Example A-16 was conducted in the same manner as in Comparative Example A-14, except that 12 µl of the pro K enzyme solution was used.

Comparative Example A-17

Comparative Example A-17 was conducted in the same manner as in Comparative Example A-14, except that the biodegradable resin (polylactic acid/PEOx) film was replaced with the biodegradable resin (polylactic acid/PEOx 20) film.

(Results)

Tables 2 and 3 show the results of the degradation percentage in one week and the transparency of the degradation liquid in each of Examples A-1 to 12 and Comparative Examples A-1 to 17.

TABLE 2

| | enzyme | degradation temperature (°C.) | biodegradable resin | solvent | percentage content (%) | SP value | degradation percentage for 1 week (%) | transparency of degradation liquid | absorbance |
|---|---|---|---|---|---|---|---|---|---|
| Example A-1 | CLE | 37 | polylactic acid/PEOx | ethanol | 4 | 12.7 | 100 | ○ | 0.010 |
| Example A-2 | CLE | 37 | polylactic acid/PEOx | ethanol | 2 | 12.7 | 100 | ○ | 0.040 |
| Example A-3 | CLE | 37 | polylactic acid/PEOx | ethanol | 7 | 12.7 | 100 | ○ | 0.004 |
| Example A-4 | CLE | 37 | polylactic acid/PEOx | ethanol | 10 | 12.7 | 58.3 | ○ | — |
| Example A-5 | CLE | 37 | polylactic acid/PEOx | hexane | 4 | 7.3 | 100 | ○ | 0.022 |
| Example A-6 | CLE | 37 | polylactic acid/PEOx | hexane | 10 | 7.3 | 100 | ○ | — |
| Example A-7 | CLE | 37 | polylactic acid/PEOx | methanol | 4 | 14.4 | 100 | ○ | 0.031 |
| Example A-8 | CLE | 37 | polylactic acid/PEOx | acetonitrile | 4 | 11.7 | 47.2 | ○ | — |
| Example A-9 | CLE | 37 | PBS | ethanol | 4 | 12.7 | 100 | ○ | — |
| Example A-10 | CLE | 37 | PBS | hexane | 4 | 7.3 | 100 | ○ | — |
| Example A-11 | pro K | 37 | polylactic acid/PEOx | ethanol | 4 | 12.7 | 100 | ○ | — |
| Example A-12 | CLE | 45 | polylactic acid/PEOx 20 | ethanol | 4 | 12.7 | 100 | ○ | 0.011 |

TABLE 3

| | | | | | | | | | |
|---|---|---|---|---|---|---|---|---|---|
| Comparative Example A-1 | CLE | 37 | polylactic acid/PEOx | ethanol | 1 | 12.7 | 100 | x | 0.240 |
| Comparative Example A-2 | CLE | 37 | polylactic acid/PEOx | ethanol | 15 | 12.7 | 8 | ○ | 0.004 |
| Comparative Example A-3 | CLE | 37 | polylactic acid/PEOx | ethanol | 20 | 12.7 | 5 | ○ | — |
| Comparative Example A-4 | CLE | 37 | polylactic acid/PEOx | ethanol | 30 | 12.7 | 4 | ○ | — |

TABLE 3-continued

| | | | | | | | | | |
|---|---|---|---|---|---|---|---|---|---|
| Comparative Example A-5 | CLE | 37 | polylactic acid/PEOx | toluene | 4 | 8.9 | 0.6 | ○ | — |
| Comparative Example A-6 | CLE | 37 | polylactic acid/PEOx | toluene | 50 | 8.9 | 3.7 | x | — |
| Comparative Example A-7 | CLE | 37 | polylactic acid/PEOx | toluene | 95 | 8.9 | 4.3 | x | — |
| Comparative Example A-8 | CLE | 37 | polylactic acid/PEOx | chloroform | 4 | 9.3 | 0 | ○ | — |
| Comparative Example A-9 | CLE | 37 | polylactic acid/PEOx | ethyl acetate | 4 | 9.6 | 0.2 | ○ | — |
| Comparative Example A-10 | CLE | 37 | polylactic acid/PEOx | isopropanol | 4 | 11.5 | 31.7 | ○ | — |
| Comparative Example A-11 | CLE | 37 | polylactic acid/PEOx | dioxane | 4 | 10 | 18.91 | ○ | — |
| Comparative Example A-12 | CLE | 37 | polylactic acid/PEOx | hexane | 1 | 7.3 | 100 | x | 0.120 |
| Comparative Example A-13 | CLE | 37 | polylactic acid/PEOx | methanol | 1 | 14.4 | 100 | x | 0.245 |
| Comparative Example A-14 | CLE | 37 | polylactic acid/PEOx | — | — | — | 100 | x | 0.363 |
| Comparative Example A-15 | CLE | 37 | PBS | — | — | — | 100 | x | 0.390 |
| Comparative Example A-16 | pro K | 37 | polylactic acid/PEOx | — | — | — | 100 | x | — |
| Comparative Example A-17 | CLE | 37 | polylactic acid/PEOx 20 | — | — | — | 50 | x | — |

* Since the transparency of the degradation liquid depends on the degradation amount, the degradation liquids of Comparative Examples in which the resin was hardly degraded were transparent.

FIG. 2 shows a HPLC chart of the degradation liquid of Example A-3. This indicated that lactic acid monomer and lactic acid oligomers were produced from the biodegradable resin (polylactic acid/PEOx).

(HPLC Measurement Conditions)

A GULLIVER series HPLC system manufactured by JASCO Corporation was used. Analysis conditions were as follows: a 5-μm, 4.6×250-mm Atlantis dC18 column manufactured by Waters was used in a column oven kept at 40° C.; a gradient mobile phase as shown in FIG. 5 was employed by using 0.5% phosphoric acid and acetonitrile at a flow rate of 1 mL/min; and 50 μl of a sample was injected. UV absorption at 210 nm was used for detection. As the standard sample, a sample obtained by purifying L-lactic acid (manufactured by Wako Pure Chemical Industries, Ltd.) was used.

From the results of Examples A-1 and 2 and Comparative Examples A-1, 2, and 3, it was found that a preferred amount of the organic solvent was such that 1%<the amount of the organic solvent<15%. It was found that when the amount of the organic solvent was 1% or less, the degradation liquid became opaque, and the recovered amount of the monomer decreased, whereas when the amount of the organic solvent was 15% or more, the degradation amount decreased extremely.

Next, FIG. 3 shows the correlation between the degradation percentage after a four-day degradation test and the SP value. In sum, it was found that a preferred SP value range of the organic solvent was such that the SP value of the organic solvent<8.5, or such that 11.5<the SP value of the organic solvent.

(IR Analysis on White Turbid Substance)

The white turbid liquid of Comparative Example 14 was centrifuged. The deposits were collected, and washed with distilled water. The collected white solid was dried under reduced pressure at 40° C. overnight, and subjected to FT-IR measurement. For the FT-IR, reflection measurement was employed (measurement frequency: 600 cm-1 to 4000 cm-1). FIG. 4 shows the results.

The peak at 1735 cm-1 is due to the carbonyl groups of polylactic acid oligomers, and the peaks at 1635 cm-1 and 1540 cm-1 are due to peptide bonds in a protein (the enzyme). In other words, it was found that the white turbidity was formed during the enzymatic degradation because deposits of aggregates of polylactic acid oligomers and the enzyme were produced.

(Experiments on Recovery Percentage of Lactic Acid Monomer)

The following experiments were conducted on Example A-1, Example A-3, Comparative Example A-1, and Comparative Example A-14 in each of which the degradation percentage after one week was 100%.

The degradation residual liquids obtained until 100% of the film was degraded were combined. The pro K enzyme solution was added thereto at a ratio of 1.2 μL/mL, and the mixture was shaken at 37° C. for one week. By using the reaction liquid and HPLC, the amount of lactic acid monomer was determined. The recovery percentage of lactic acid monomer was calculated as follows: the amount of lactic acid monomer/the amount of polylactic acid fed×100. Table 4 shows the results.

TABLE 4

| | recovery percentage of lactic acid monomer (%) |
|---|---|
| Example A-1 | 100 |
| Example A-3 | 100 |
| Comparative Example A-1 | 34 |
| Comparative Example A-14 | 26 |

2. Examples B-1 to 8 and Comparative Examples B-1 to 10 were conducted as follows.

The hydrolase solutions used were prepared as follows.

Pro K (Proteinase K) Enzyme Solution

A pro K (Proteinase K) enzyme solution was prepared by dissolving 20 mg of a powder of Tritirachium album-derived Proteinase K (Wako Pure Chemical Industries, Ltd.) in 1 ml of a 0.05 M Tris-HCl buffer solution (pH 8.0) containing 50 w/w % of glycerin.

CLE Enzyme Solution

A *Cryptococcus* sp. S-2-derived lipase CS2 (Japanese Patent Application Publication No. 2004-73123) enzyme solution having a lipase activity of 653 U/mL provided by National Research Institute of Brewing was used. The lipase activity was measured by using para-nitrophenyl laurate as the substrate. Here, 1 U of the lipase activity is defined as the amount of enzyme with which para-nitrophenol is liberated from para-nitro phenyl laurate at 1 μmol/min.

(Measurement of Glass Transition Temperature)

The glass transition temperature (Tg) was measured by using DSC 6220 manufactured by Seiko Instruments Inc. (differential scanning calorimetry). As for measurement conditions, the measurement was conducted in a nitrogen atmosphere at a rate of temperature rise of 10° C./min from 0 to 200° C. The samples used were PEOx and PEOx 20 to be described later, and the amount of each sample was 5 to 10 mg.

Synthesis of Polyethylene Oxalate (PEOx) (Aliphatic Polyester (B'))

Into a 300-mL separable flask equipped with a mantle heater, a stirrer, a nitrogen inlet, and a condenser, 354 g (3.0 mol) of dimethyl oxalate, 223.5 g (3.6 mol) of ethylene glycol, and 0.30 g of tetrabutyl titanate were introduced. The flask was heated under nitrogen stream from 110° C. until the inside temperature reached 170° C., while methanol was being distilled off. Thus, the reaction was conducted for 9 hours. At the end, 210 ml of methanol was distilled off. Thereafter, stirring was performed for 1 hour at an inside temperature of 150° C. and at a reduced pressure of 0.1 to 0.5 mmHg. After a 7-hour reaction at an inside temperature of 170° C. to 190° C., the viscosity increased, and the product was taken out. The η inh of the synthesized product was 0.12.

The solution viscosity (η inh) was measured as follows. Specifically, the synthesized polyethylene oxalate that had been vacuum-dried at 120° C. overnight was used. The polyethylene oxalate was immersed in a mixture solvent of m-chlorophenol/1,2,4-trichlorobenzene=4/1 (weight ratio) and dissolved thereinto at 150° C. in approximately 10 minutes to prepare a solution at a concentration of 0.4 g/dl. Thereafter, the solution viscosity was measured at 30° C. by use of an Ubbelohde viscometer (Unit: dl/g).

Synthesis of Polyoxalate (PEOx 20))

The polyoxalate (PEOx 20) was synthesized by the same method as in the above-described synthesis of PEOx, except that 94.5 g (0.8 mol) of dimethyl oxalate and 38.8 g (0.2 mol) of dimethyl terephthalate were used instead of 354 g (3.0 mol) of dimethyl oxalate.

GPC measurement showed that the weight average molecular weight (Mw) of the PEOx 20 was 20000. The GPC used was HLC-8120 manufactured by Tosoh Corporation, the columns used were two TSK gel Super HM-H columns, and the guard column used was a TSK guard column Super H-H column. The temperature of a column oven was set to 40° C. Chloroform was used as an eluent, and the flow rate thereof was set to 0.5 ml/min. The amount of sample injected was 15 μl. Polystyrene dissolved in chloroform was used as a standard. As for sample preparation, chloroform was used as a solvent with a sample concentration of 5 mg/ml, and the sample was filtered before use.

(Properties of PEOx and PEOx 20)

The monomer, oxalic acid, shows a pH of 1.6 at a concentration of 0.005 g/ml. The PEOx and the PEOx 20 release, upon hydrolysis, oxalic acid or oxalic acid oligomers in an aqueous solution.

Monomer Content and Glass Transition Temperature of Polyoxalate

|  | dimethyl oxalate (mol) | terephthalic acid (mol) | ethylene glycol (mol) | Tg (° C.) |
|---|---|---|---|---|
| PEOx | 3 | 0 | 3.6 | 25 |
| PEOx 20 | 0.8 | 0.2 | 1.2 | 45 |

Fabrication of Readily Degradable Resin Composition Film (Aliphatic Polyester (A)+Aliphatic Polyester (B'))

Master pellets of polylactic acid (manufactured by NatureWorks LLC)/PEOx or PEOx 20=95/5 mass % were prepared by using a twin-screw extruder (manufactured by Technovel Corporation) at a melt blending temperature of 200° C. The obtained pellets were formed into a 100-μm readily degradable resin composition film by using Labo Plastomill (manufactured by Toyo Seiki Seisaku-sho, Ltd.) at a film formation temperature of 200° C.

Example B-1

(a) Measurement of Enzyme Activity of Protease on Biodegradable Film (Simple Polymer of Aliphatic Polyester (A) Component)

Into each of 60 mM phosphate buffer solutions (11 kinds in a pH range of 4.7 to 9.0) which were each 10 ml in volume, and which were prepared as degradation liquids by adding 12 μl of the pro K enzyme solution thereto, the polylactic acid film (having a thickness of 100 μm) cut into 2 cm×2 cm (45 mg) was immersed, and the mixture was shaken at 37° C. and 100 rpm for 4 days. The degradation amount (mg) after 4 days was employed as a film degradation activity value. Here, the degradation amount after 4 days was a value represented as follows: the film weight (mg) at the beginning of the degradation−the film weight (mg) after 4 days. In addition, for the film weight measurement, values obtained by measurement after drying the film in a dryer at 45° C. overnight were employed. The film degradation activities in the phosphate buffer solutions with the various pHs were as follows.

TABLE 5

| pH | 4.7 | 5.5 | 6.0 | 6.5 | 7.0 | 7.2 | 7.5 | 7.8 | 8.0 | 8.5 | 9.0 |
|---|---|---|---|---|---|---|---|---|---|---|---|
| activity | 1.6 | 5.09 | 9.13 | 7.15 | 3.59 | 3.15 | 2.34 | 2.33 | 2.57 | 2.21 | 2.08 |

(b) Specifying Active pH Range

As can be seen from Table 1 above and FIG. 6 in which the contents thereof are illustrated, the maximum activity value of the protease on the polylactic acid film was 9.13 which was obtained when the 60 mM phosphate buffer solution of pH 6.0 was used. A range of pH 5.0 to pH 7.2 in which the activity value was not less than 2.7, which was not less than 30% of the maximum activity value, was determined as the active pH range for use of the protease.

(c) Degradation of Readily Degradable Resin Composition (Resin Composition Containing Aliphatic Polyester (A) and Aliphatic Polyester (B'))

Into 10 ml of a 60 mM phosphate buffer solution of pH 7.2 prepared as a degradation liquid by adding 12 μl of the pro K enzyme solution, the readily degradable resin composition film {the aliphatic polyester (B') was the PEOx} cut into 2 cm×2 cm (weight: 45 mg) was immersed, and the mixture was shaken at 37° C. and 100 rpm for 7 days. To avoid a decrease in pH, the 7 days was divided into 2 days, 2 days, and 3 days, between which the degradation liquid was replaced.

Example B-2

Example B-2 was conducted under the same conditions as those employed in Example B-1, except that a 60 mM phosphate buffer solution of pH 7.0 was used in the step (C) of Example 1. (Since the same readily degradable resin composition as Example 1 was used, the active pH range was the same, namely, pH 5.0 to pH 7.2.)

Example B-3

Example B-3 was conducted under the same conditions as those employed in Example B-1, except that a 60 mM phosphate buffer solution of pH 6.5 was used in the step (C) of Example 1. (Since the same readily degradable resin composition as Example B-1 was used, the active pH range was the same, namely, pH 5.0 to pH 7.2.)

Example B-4

Example B-4 was conducted in the same manner as in the step (c) of Example B-1, except that distilled water was used instead of the phosphate buffer solution and that 22.5 mg of calcium carbonate (Wako Pure Chemical Industries, Ltd.) was added as the neutralizing agent. (Since the same readily degradable resin composition as that of Example B-1 was used, the active pH range was the same, namely, pH 5.0 to pH 7.2.) The final pH was 6.5.

Comparative Example B-1

Comparative Example B-1 was conducted under the same conditions as those employed in Example B-1, except that a 60 mM phosphate buffer solution of pH 9 was used in the step (C) of Example B-1. (Since the same readily degradable resin composition as Example B-1 was used, the active pH range was the same, namely, pH 5.0 to pH 7.2.)

Comparative Example B-2

Comparative Example B-2 was conducted under the same conditions as those employed in Example 1, except that a 60 mM phosphate buffer solution of pH 8.0 was used in the step (C) of Example B-1. (Since the same readily degradable resin composition as Example B-1 was used, the active pH range was the same, namely, pH 5.0 to pH 7.2.)

Comparative Example B-3

Into 10 ml of a 60 mM phosphate buffer solution of pH 6.5 prepared as a degradation liquid by adding 12 μl of the pro K enzyme solution, the readily degradable resin composition film cut into 2 cm×2 cm (weight: 45 mg) was immersed, and the mixture was shaken at 37° C. and 100 rpm for 7 days. The enzyme solution was not replaced. (Since the same readily degradable resin composition as Example B-1 was used, the active pH range was the same, namely, pH 5.0 to pH 7.2.)

Comparative Example B-4

Comparative Example B-4 was conducted under the same conditions as those employed in Example 1, except that a 60 mM phosphate buffer solution of pH 4.7 was used in the step (C) of Example B-1. (Since the same readily degradable resin composition as Example B-1 was used, the active pH range was the same, namely, pH 5.0 to pH 7.2.)

FIG. 7 shows the fluctuation in pH in Examples B-1 to 4 and Comparative Examples B-1 to 4. In addition, the following Table 6 shows the results of degradation of the readily degradable resin composition.

TABLE 6

| | aliphatic polyester B' | temperature (° C.) | enzyme solution | initial pH | at the beginning of the degradation of enzyme activity (pH 5.0 to 7.2) | acid catalyst effect (pH < 8.0) | amount of weight reduction (mg) | | | replacement of degradation liquid |
|---|---|---|---|---|---|---|---|---|---|---|
| | | | | | | | after 2 days | after 4 days | after 7 days | |
| Example B-1 | PEOx | 37 | pro K 12 μl | 7.2 | ○ | ○ | 2.84 | 9.06 | 21.96 | yes |
| Example B-2 | PEOx | 37 | pro K 12 μl | 7 | ○ | ○ | 2.77 | 9.66 | 21.18 | yes |
| Example B-3 | PEOx | 37 | pro K 12 μl | 6.5 | ○ | ○ | 4.42 | 15.07 | disappear | yes |
| Example B-4 | PEOx | 37 | pro K 12 μl | 7.2 | ○ | ○ | 23.03 | disappear | disappear | no (with neutralizing agent) |
| Comparative Example B-1 | PEOx | 37 | pro K 12 μl | 9 | x | x | 1.92 | 5.58 | 12 | yes |
| Comparative Example B-2 | PEOx | 37 | pro K 12 μl | 8 | ○ | x | 0 | 3.06 | 10.13 | yes |
| Comparative Example B-3 | PEOx | 37 | pro K 12 μl | 6.5 | ○ | ○ | 14.03 | 15.78 | 18.62 | no (final pH 4.2) |
| Comparative Example B-4 | PEOx | 37 | pro K 12 μl | 4.7 | x | ○ | 2.98 | 4.03 | 4.79 | yes |

Cases where the pH of the degradation liquid was always within the pH range of 5 to 7.2 in which the enzyme was active during the degradation process are represented by ○, and other cases are represented by x.

As for the acid catalyst effect, items with pH 8 or less are represented by ○, and items with pH 8 or more are represented by x.

Example B-5

(a) Measurement of Enzyme Activity of Lipase CS2 on Biodegradable Film (Simple Polymer of Aliphatic Polyester (A))

Into each of 60 mM phosphate buffer solutions (11 kinds in a pH range of 3.0 to 8.0) which were each 10 ml in volume, and which were prepared as degradation liquids by adding 48 μl of the CLE enzyme solution thereto, the polylactic acid film (having a thickness of 100 μm) cut into 2 cm×2 cm (45 mg) was immersed, and the mixture was shaken at 37° C. and 100 rpm for 4 days. The degradation amount (mg) after 4 days was employed as a film degradation activity value. Here, the degradation amount after 4 days was a value represented as follows: the film weight (mg) at the beginning of the degradation−the film weight (mg) after 4 days. In addition, for the film weight measurement, values obtained by measurement after drying the film in a dryer at 45° C. overnight were employed. The film degradation activities in the phosphate buffer solutions of the various pHs were as follows.

TABLE 7

| pH | 3.0 | 3.7 | 4.7 | 5.5 | 6.0 | 6.5 | 7.0 | 7.2 | 7.5 | 7.8 | 8.0 |
|---|---|---|---|---|---|---|---|---|---|---|---|
| activity | 0 | 1 | 6.05 | 6.13 | 9.33 | 9 | 15.08 | 14.48 | 12.78 | 9.73 | 0.11 |

(b) Specifying Active pH Range

As can be seen from Table 3 above and FIG. 8 in which the contents thereof are illustrated, the maximum activity value of lipase CS2 on the polylactic acid film was 15 which was obtained when the 60 mM phosphate buffer solution of pH 7.0 was used. A range of pH 4.4 to pH 7.8 in which the activity value was not less than 4.5, which was not less than 30% of the maximum activity value, was determined as the active pH range for use of lipase CS2.

(c) Degradation of Readily Degradable Resin Composition (Resin Composition Containing Aliphatic Polyester (A) and Aliphatic Polyester (B'))

Into each of 60 mM phosphate buffer solutions of pH 7.0 which were each 10 ml in volume, and which were prepared as degradation liquids by adding 48 μl of the CLE enzyme solution thereto, the readily degradable resin composition film {containing the PEOx as the aliphatic polyester (B')} cut into 2 cm×2 cm (weight: 45 mg) was immersed, and the mixture was shaken at 37° C. and 100 rpm for 7 days. To avoid a decrease in pH, the 7 days was divided into 2 days, 2 days, and 3 days, between which the degradation liquid was replaced.

Example B-6

Example B-6 was conducted under the same conditions as those employed in Example B-5, except that a 60 mM phosphate buffer solution of pH 6.5 was used in the step (C) of Example B-5. (Since the same readily degradable resin composition as Example B-5 was used, the active pH range was the same, namely, pH 4.4 to pH 7.8.)

Example B-7

Example B-7 was conducted under the same conditions as those employed in Example B-5, except that a 60 mM phosphate buffer solution of pH 7.5 was used in the step (C) of Example B-5 (Since the same readily degradable resin composition as Example B-5 was used, the active pH range was the same, namely, pH 4.4 to pH 7.8.)

Example B-8

Example B-8 was conducted in the same manner as Example 5, except that the readily degradable resin composition film {containing the PEOx 20 as the aliphatic polyester (B')} was used instead, and that the temperature was changed to 45° C. The initial pH was 7, and the final pH was 4.5, indicating that the degradation was carried out within the active pH range.

Comparative Example B-5

Comparative Example B-5 was conducted under the same conditions as those employed in Example B-5, except that a 60 mM phosphate buffer solution of pH 8 was used in the step (C) of Example 5. (Since the same readily degradable resin composition as Example B-5 was used, the active pH range was the same, namely, pH 4.4 to pH 7.8.)

Comparative Example B-6

Comparative Example B-6 was conducted under the same conditions as those employed in Example B-5, except that a 60 mM phosphate buffer solution of pH 9 was used in the step (C) of Example B-5. (Since the same readily degradable resin composition as Example B-5 was used, the active pH range was the same, namely, pH 4.4 to pH 7.8.)

Comparative Example B-7

Comparative Example B-7 was conducted under the same conditions as those employed in Example B-5, except that a 60 mM phosphate buffer solution of pH 4.7 was used in the step (C) of Example B-5. (Since the same readily degradable resin composition as Example B-5 was used, the active pH range was the same, namely, pH 4.4 to pH 7.8.)

Comparative Example B-8

Comparative Example B-8 was conducted under the same conditions as those employed in Example B-5, except that a 60 mM phosphate buffer solution of pH 3.7 was used in the step (C) of Example B-5. (Since the same readily degradable resin composition as Example B-5 was used, the active pH range was the same, namely, pH 4.4 to pH 7.8.)

Comparative Example B-9

Comparative Example B-9 was conducted under the same conditions as those employed in Example B-5, except that a 60 mM phosphate buffer solution of pH 3.0 was used in the step (C) of Example B-5. (Since the same readily degradable resin composition as Example B-5 was used, the active pH range was the same, namely, pH 4.4 to pH 7.8.)

Comparative Example B-10

Comparative Example B-10 was conducted in the same manner as Example 5, except that the readily degradable resin composition film {containing the PEOx 20 as the aliphatic polyester (B')} was used instead. The initial pH was 7, and the final pH was 5.1, indicating that the degradation was carried out within the active pH range.

FIG. 9 shows the fluctuation in pH in Examples B-5 to 7 and Comparative Examples B-5 to 9. In addition, the following Table 8 shows the results of degradation of the readily degradable resin composition.

CLE Enzyme Reaction Liquid

A *Cryptococcus* sp. S-2-derived lipase CS2 (Japanese Patent Application Publication No. 2004-73123) enzyme reaction liquid having a lipase activity of 653 U/mL and provided by National Research Institute of Brewing was used. The lipase activity was measured by using para-nitro phenyl laurate as the substrate. Here, 1 U of the lipase activity is defined as the amount of enzyme with which para-nitro-phenol is liberated from para-nitro phenyl laurate at 1 μmol/min.

(Measurement of Glass Transition Temperature)

The glass transition temperature (Tg) was measured by using DSC 6220 manufactured by Seiko Instruments Inc. (differential scanning calorimetry). As for measurement conditions, the measurement was conducted in a nitrogen atmosphere at a rate of temperature rise of 10° C./min from 0 to 200° C. The samples used were PEOx and PEOx 20 to be described later, and the amount of each sample was 5 to 10 mg.

TABLE 8

| | aliphatic polyester B' | temperature (° C.) | enzyme solution | initial pH | at the beginning of the degradation of enzyme activity (pH 4.4 to 7.8) | acid catalyst effect (pH < 8.0) | amount of weight reduction (mg) after 2 days | after 4 days | after 7 days | replacement of degradation liquid |
|---|---|---|---|---|---|---|---|---|---|---|
| Example B-5 | PEOx | 37 | CLE 48 μl | 7 | ○ | ○ | 18.87 | 38.13 | disappear (within 7 days) | yes |
| Example B-6 | PEOx | 37 | CLE 48 μl | 6.5 | ○ | ○ | 24.72 | 29.35 | disappear (within 7 days) | yes |
| Example B-7 | PEOx | 37 | CLE 48 μl | 7.5 | ○ | ○ | 15.26 | 37.64 | disappear (within 7 days) | yes |
| Example B-8 | PEOx 20 | 45 | CLE 48 μl | 7 | ○ | ○ | 27.5 | disappear | | yes |
| Comparative Example B-5 | PEOx | 37 | CLE 48 μl | 8 | x | x | 3.23 | 15.14 | 36.89 | yes |
| Comparative Example B-6 | PEOx | 37 | CLE 48 μl | 9 | x | x | 0.24 | 0.96 | 1.48 | yes |
| Comparative Example B-7 | PEOx | 37 | CLE 48 μl | 4.7 | ○ | ○ | 7.34 | 13.94 | 19.44 | yes (pH 3.8 to 4.7) |
| Comparative Example B-8 | PEOx | 37 | CLE 48 μl | 3.7 | x | ○ | 4.29 | 6.1 | 8.91 | yes |
| Comparative Example B-9 | PEOx | 37 | CLE 48 μl | 3 | x | ○ | 3.05 | 2.75 | 3.51 | yes |
| Comparative Example B-10 | PEOx 20 | 37 | CLE 48 μl | 7 | ○ | ○ | 5.83 | 20.04 | disappear (within 7 days) | yes |

Cases where the pH of the degradation liquid was always within the pH range of 4.4 to 7.8 in which the enzyme was active during the degradation process are represented by ○, and other cases are represented by x.

As for the acid catalyst effect, items with pH 8 or less are represented by ○, and items with pH 8 or more are represented by x.

3. Examples C-1 to 5 and Comparative Examples C-1 to 4 were conducted as follows.

The enzyme reaction liquids of degradation enzymes used were prepared as follows.

Pro K (Proteinase K) Enzyme Reaction Liquid

A pro K (Proteinase K) enzyme reaction liquid was prepared by dissolving 20 mg of a powder of Tritirachium album-derived Proteinase K (manufactured by Wako Pure Chemical Industries, Ltd.) in 1 ml of a 0.05 M Tris-HCl buffer solution (pH 8.0) containing 50 w/w % of glycerin.

Synthesis of Polyethylene Oxalate (PEOx) (Aliphatic Polyester (B'))

Into a 300-mL separable flask equipped with a mantle heater, a stirrer, a nitrogen inlet, and a condenser, 354 g (3.0 mol) of dimethyl oxalate, 223.5 g (3.6 mol) of ethylene glycol, and 0.30 g of tetrabutyl titanate were introduced. The flask was heated under nitrogen stream from 110° C. until the inside temperature reached 170° C., while methanol was being distilled off. Then, the reaction was conducted for 9 hours. At the end, 210 ml of methanol was distilled off. Thereafter, stirring was performed for 1 hour at an inside pressure of 150° C. and at a reduced pressure of 0.1 to 0.5 mmHg. After a 7-hour reaction at an inside temperature of 170° C. to 190° C., the viscosity increased, and the product was taken out. The η inh of the synthesized product was 0.12.

The solution viscosity (η inh) was measured as follows. Specifically, the synthesized polyethylene oxalate which had been vacuum-dried at 120° C. overnight was used. The polyethylene oxalate was immersed in a mixture solvent of m-chlorophenol/1,2,4-trichlorobenzene=4/1 (weight ratio), and dissolved thereinto at 150° C. in approximately 10 minutes to prepare a solution at a concentration of 0.4 g/dl. Thereafter, the solution viscosity was measured at 30° C. by use of an Ubbelohde viscometer (Unit: dl/g).

In addition, the pH of an aqueous solution obtained by dissolving oxalic acid, which was the monomer of the above-described polyethylene oxalate, at a concentration of 0.005 g/ml was 1.6.

Synthesis of Polyoxalate (PEOx 20))

Polyoxalate (PEOx 20) was synthesized in the same manner as in the above-described synthesis of PEOx, except that 94.5 g (0.8 mol) of dimethyl oxalate and 38.8 g (0.2 mol) of dimethyl terephthalate were used instead of 354 g (3.0 mol) of dimethyl oxalate.

GPC measurement showed that the weight average molecular weight (Mw) was 20000. The GPC used was HLC-8120 manufactured by Tosoh Corporation, and the columns used were two TSK gel Super HM-H columns, and the guard column used was a TSK guard column Super H-H column. The temperature of a column oven was set to 40° C. Chloroform was used as an eluent, and the flow rate was set to 0.5 ml/min. The amount of sample injected was 15 μl. Polystyrene dissolved in chloroform was used as a standard. As for sample preparation, chloroform was used as a solvent with a sample concentration of 5 mg/ml, and the sample was filtered before use.

(Properties of PEOx and PEOx 20)

The monomer, oxalic acid, shows a pH of 1.6 at a concentration of 0.005 g/ml. The PEOx and the PEOx 20 release, upon hydrolysis, oxalic acid or oxalic acid oligomers in an aqueous solution.

Monomer Content and Glass Transition Temperature of Polyoxalate

|  | dimethyl oxalate (mol) | terephthalic acid (mol) | ethylene glycol (mol) | Tg (° C.) |
|---|---|---|---|---|
| PEOx | 3 | 0 | 3.6 | 25 |
| PEOx 20 | 0.8 | 0.2 | 1.2 | 45 |

Fabrication of Readily Degradable Resin Composition Film (Aliphatic Polyester (A)+Aliphatic Polyester (B'))

Master pellets of polylactic acid (4032D manufactured by NatureWorks LLC)/PEOx or PEOx 20=95/5 mass % were melt blended by using a twin-screw extruder (manufactured by TECHNOVEL CORPORATION) at 200° C. Then, readily degradable resin composition films of 100 μm and of 250 μm were formed by using Labo Plastomill (manufactured by Toyo Seiki Seisaku-sho, Ltd.).

Specifying Active pH Range of Protease K
(a) Measurement of Enzyme Activity of Protease K on Biodegradable Film (Simple Polymer of Aliphatic Polyester (A) Component)

Into each of 60 mM phosphate buffer solutions (11 kinds in a pH range of 4.7 to 9.0) which were each 10 ml in volume, and which were prepared as degradation liquids by adding 12 μl of the pro K enzyme solution thereto, the polylactic acid film (having a thickness of 100 μm) cut into 2 cm×2 cm (45 mg) was immersed, and the mixture was shaken at 37° C. and 100 rpm for 4 days. The degradation amount (mg) after 4 days was employed as a film degradation activity value. Here, the degradation amount after 4 days was a value represented as follows: the film weight (mg) at the beginning of the degradation–the film weight (mg) after 4 days. In addition, for the film weight measurement, values obtained by measurement after drying the film in a dryer at 45° C. overnight were employed. The film degradation activities in the phosphate buffer solutions of the various pHs were as follows.

TABLE 9

| pH | 4.7 | 5.5 | 6.0 | 6.5 | 7.0 | 7.2 | 7.5 | 7.8 | 8.0 | 8.5 | 9.0 |
|---|---|---|---|---|---|---|---|---|---|---|---|
| activity | 1.6 | 5.09 | 9.13 | 7.15 | 3.59 | 3.15 | 2.34 | 2.33 | 2.57 | 2.21 | 2.08 |

(b) Specifying Active pH Range of Protease K

As can be seen from the above-described Table 1 and FIG. 10 in which the contents thereof are illustrated, the maximum activity value of protease K on the polylactic acid film was 9.13 which was obtained when the 60 mM phosphate buffer solution of pH 6.0 was used. A range of pH 5.0 to pH 7.2 in which the activity value was not less than 2.7, which was not less than 30% of the maximum activity value, was determined as the active pH range for use of protease K.

Specifying Active pH Range of Lipase CS2
(a) Measurement of Enzyme Activity of Lipase CS2 on Biodegradable Film (Simple Polymer of Aliphatic Polyester (A))

Into each of 60 mM phosphate buffer solutions (11 kinds in a pH range of 3.0 to 8.0) which were each 10 ml in volume, and which were prepared as degradation liquids by adding 48 μl of the CLE enzyme solution thereto, the polylactic acid film (having a thickness of 100 μm) cut into 2 cm×2 cm (45 mg) was immersed, and the mixture was shaken at 37° C. and 100 rpm for 4 days. The degradation amount (mg) after 4 days was employed as a film degradation activity value. Here, the degradation amount after 4 days was a value represented as follows: the film weight (mg) at the beginning of the degradation–the film weight (mg) after 4 days. In addition, for the film weight measurement, values obtained by measurement after drying the film in a dryer at 45° C. overnight were employed. The film degradation activities in the phosphate buffer solutions of the various pHs were as follows.

TABLE 10

| pH | 3.0 | 3.7 | 4.7 | 5.5 | 6.0 | 6.5 | 7.0 | 7.2 | 7.5 | 7.8 | 8.0 |
|---|---|---|---|---|---|---|---|---|---|---|---|
| activity | 0 | 1 | 6.05 | 6.13 | 9.33 | 9 | 15.08 | 14.48 | 12.78 | 9.73 | 0.11 |

(b) Specifying Active pH Range of Lipase CS2

As can be seen from the above-described Table 2 and FIG. 11 in which the contents thereof are illustrated, the maximum activity value of Lipase CS2 on the polylactic acid film was 15 which was obtained when the 60 mM phosphate buffer solution of pH 7.0 was used. A range of pH 4.4 to pH 7.8 in which the activity value was not less than 4.5, which was not less than 30% of the maximum activity value, was determined as the active pH range for use of Lipase CS2.

Example C-1

Into a 50-ml Falcon tube, the readily degradable resin composition film (in which the PEOx was used as the aliphatic polyester B') cut into 2 cm×2 cm (90 mg in weight and 250 μm in thickness), 30 ml of distilled water (neutral) were added. Moreover, 36 μl of the pro K enzyme solution and calcium carbonate (manufactured by Wako Pure Chemical Industries, Ltd., particle diameter: 10 to 15 μm) in an amount of 0.5 times the film weight were added thereto. The reaction was conducted at 37° C. and 200 rpm for one week.

Example C-2

Into a 3-L water bath equipped with a temperature controller, a heater, and a stirrer, the readily degradable resin composition films (20 sheets, total weight: 12 g, thickness: 250 μm) cut into 5 cm×5 cm, and 3 L of distilled water (neutral) were introduced. Moreover, 15 ml of the CLE enzyme solution, and chitosan (chitosan 50 manufactured by Wako Pure Chemical Industries, Ltd., particle diameter: 30 to 300 μm) in an amount of 1.5 times the film weight were added thereto. The reaction was conducted at 37° C. and 500 rpm for one week.

Example C-3

Example C-3 was conducted in the same manner as in Example C-2, except that chitosan was replaced with calcium carbonate.

Example C-4

Into a 25-ml glass vial, the readily degradable resin composition film (in which the PEOx 20 was used as the aliphatic polyester B') cut into 2 cm×2 cm (70 mg in weight and 150 μm in thickness), 10 ml of distilled water (neutral) were added. Moreover, 48 μl of the CLE enzyme solution and calcium carbonate (manufactured by Wako Pure Chemical Industries, Ltd., particle diameter: 10 to 15 μm) in an amount of 0.5 times the film weight were added thereto. The reaction was conducted at 45° C. and 100 rpm for one week.

Comparative Example C-1

Comparative Example C-1 was conducted in the same manner as in Example C-1, except that no calcium carbonate was added.

Comparative Example C-2

Comparative Example C-2 was conducted in the same manner as in Example C-3, except that no calcium carbonate was added.

Comparative Example C-3

Comparative Example C-3 was conducted in the same manner as in Example 4, except that the degradation temperature was changed to 37° C.

TABLE 11

| | aliphatic polyester B' | temperature (° C.) | enzyme solution | neutralizing agent | film weight | initial pH | final pH | amount of weight reduction (reduction percentage) | | |
|---|---|---|---|---|---|---|---|---|---|---|
| | | | | | | | | after 2 days | after 4 days | after 7 days |
| Example C-1 | PEOx | 37 | pro K | calcium carbonate | 90 mg | 7.16 | 6.65 | 28.96 mg (−32.2%) | 52.79 mg (−58.7%) | 77.05 mg (−85.6%) |
| Example C-2 | PEOx | 37 | CLE | chitosan | 12 g | 6.3 | 5.2 | — | — | 5.12 g (−42.7%) |
| Example C-3 | PEOx | 37 | CLE | calcium carbonate | 12 g | 7.5 | 6.5 | — | — | 4.56 g (−38.0%) |
| Example C-4 | PEOx 20 | 45 | CLE | calcium carbonate | 70 mg | 7.16 | 6 | 68.14 mg (−97.3%) | disappear | |
| Comparative Example C-1 | PEOx | 37 | pro K | none | 90 mg | 7.0 | 3.6 | 0 (−0%) | 0.43 mg (−0.5%) | 1.74 mg (−1.9%) |
| Comparative Example C-2 | PEOx | 37 | CLE | none | 12 g | 7.0 | 4.93 | — | — | 0.57 g (−4.8%) |
| Comparative Example C-3 | PEOx 20 | 37 | CLE | calcium carbonate | 70 mg | 7.16 | 6.7 | 23.11 mg (−33%) | 43.61 mg (−62.3%) | 62.71 mg (−89.6%) |

From the results of Examples C-1 to 3 and Comparative Examples C-1 and 2, it was found that when the acid neutralizing agent was added to the degradation liquid, the degradation amount increased because the decrease in pH was successfully inhibited, and thus the enzyme activity was maintained. In addition, from the results of Example 4 and Comparative Example 3, it was found that the degradation amount increased by setting the degradation temperature to a value not lower than the glass transition temperature of the aliphatic polyester B'.

Next, the following experiments were carried out to examine the degradation performances with an acid neutralizing agent incompatible with water and with an acid neutralizing agent compatible with water.

Example C-5

Into a 25-ml glass vial, the readily degradable resin composition film cut into 2 cm×2 cm (45 mg in weight and 100 μm in thickness), 10 ml of distilled water (neutral) were added. Moreover, 12 μl of the pro K enzyme solution and calcium carbonate in an amount of 0.5 times the film weight were added thereto. The reaction was conducted at 37° C. and 100 rpm for one week.

Comparative Example C-4

Into a 25-ml vial, the readily degradable resin composition film cut into 2 cm×2 cm (weight: 45 mg, thickness: 100 μm) and a degradation liquid (pH: 7.0, 10 ml of the phosphate buffer solution and 12 μl of the pro K enzyme solution) were added. The reaction was conducted at 37° C. and 100 rpm for one week, and the degradation liquid was replaced at intervals of 2 days, 2 days, and 3 days.

TABLE 12

| | aliphatic polyester B' | temperature (° C.) | enzyme solution | neutralizing agent | film weight | initial pH | final pH | amount of weight reduction (reduction percentage) | | |
|---|---|---|---|---|---|---|---|---|---|---|
| | | | | | | | | after 2 days | after 4 days | after 7 days |
| Example C-5 | PEOx | 37 | pro K | calcium carbonate | 45 mg | 7.16 | 6.5 | 23.03 mg (−51.2%) | disappear (4 days) (−100%) | disappear (4 days) (−100%) |
| Comparative Example C-4 | PEOx | 37 | pro K | (60 mM phosphate buffer solution) | 45 mg | 7.2 | 6.85 | 2.84 mg (−6.3%) | 9.06 mg (−20.1%) | 21.96 mg (−47.1%) |

These results indicated that when a comparison was made between the acid neutralizing agent incompatible with water and the acid neutralizing agent compatible with water, the acid neutralizing agent incompatible with water acted more effectively. This indicated that the compatible acid neutralizing agent of Comparative Example C-3 entered the inside of the readily degradable resin composition, and neutralized the acid, so that the degradation performances were deteriorated.

Figure 1:
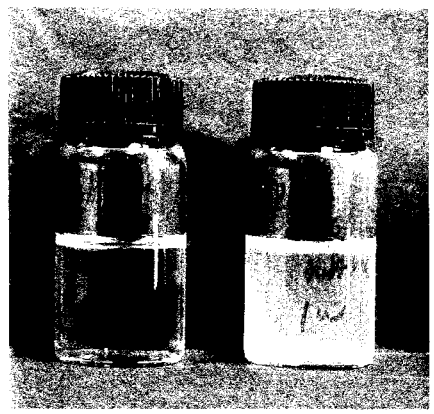
FIG. 1 is a photograph in which the transparency is compared between Example A-1 (left) and Comparative Example A-14 (right).
Figure 2:
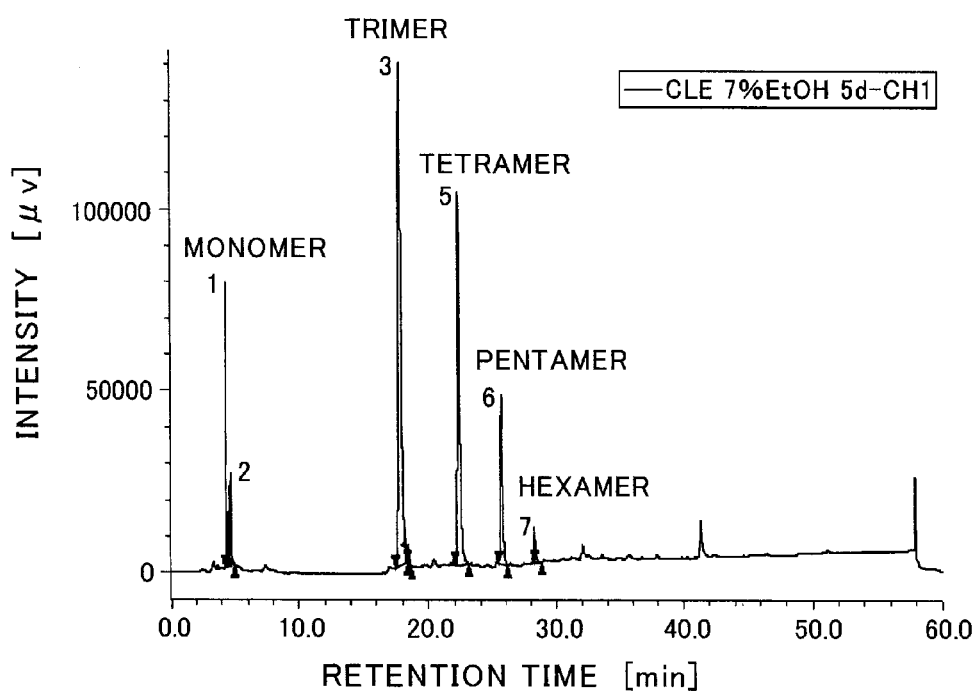
FIG. 2 is an HPLC chart of Example A-3.
Figure 3:
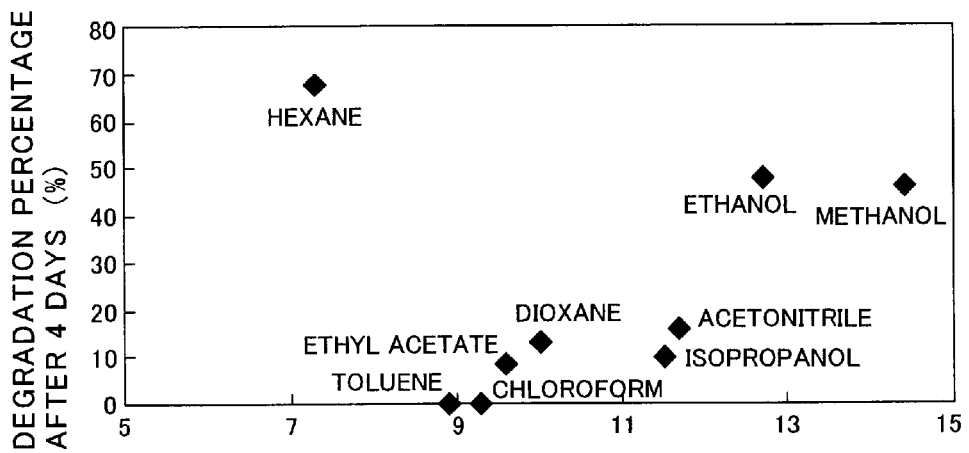
FIG. 3 is a graph showing a correlation between the degradation percentage after a 4-day degradation test and the SP value.
Figure 4:
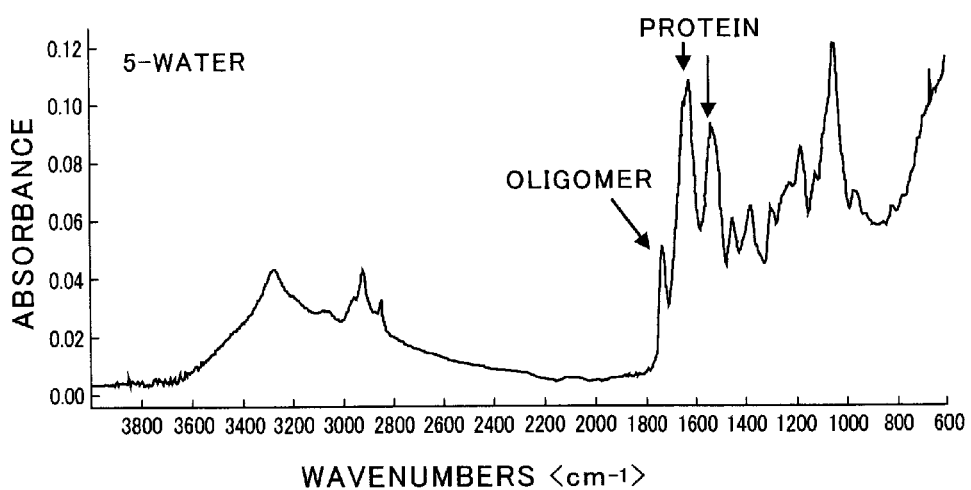
FIG. 4 is a graph showing FT-IR of a white turbid substance.
Figure 5:
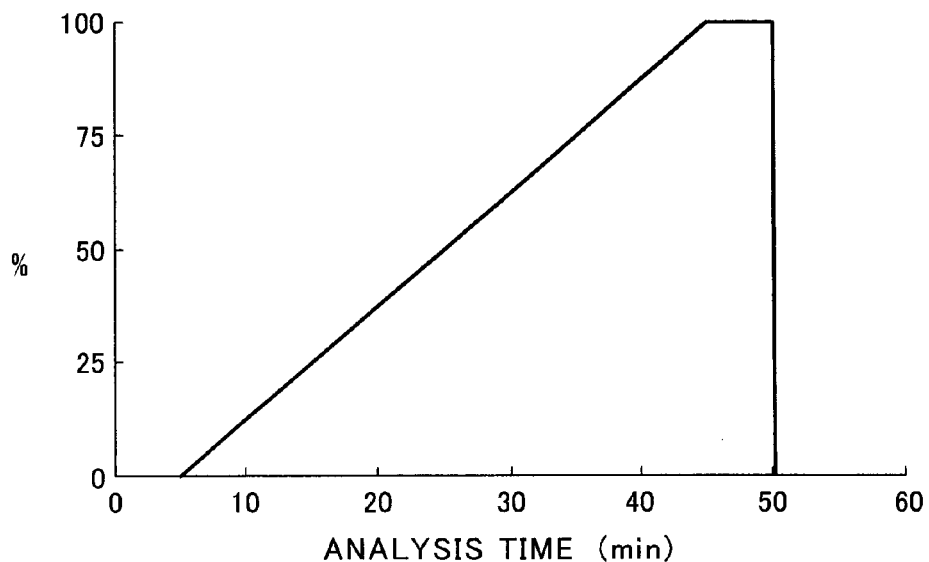
FIG. 5 is a graph showing HPLC measurement conditions.
Figure 6:
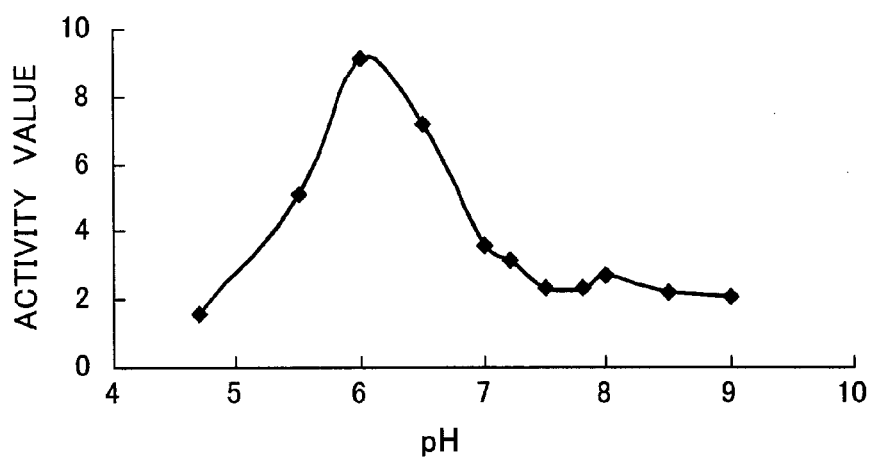
FIG. 6 shows degradation activity of pro K on polylactic acid film.
Figure 7:
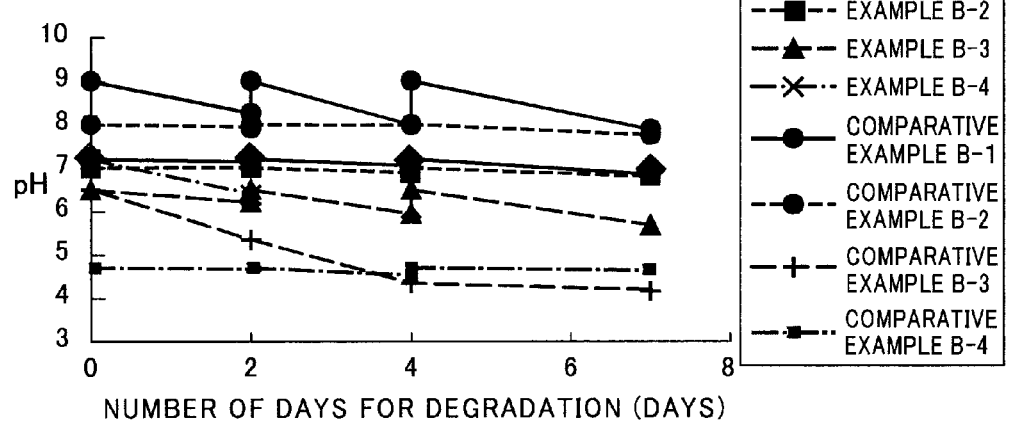
FIG. 7 shows change with time in pH in a case where a readily degradable resin composition was degraded in an enzyme solution of pro K.
Figure 8:
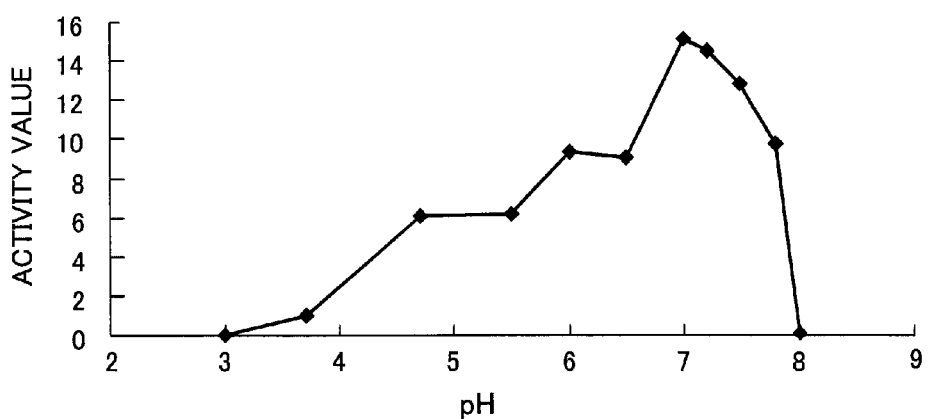
FIG. 8 shows a degradation activity of CLE on polylactic acid film.
Figure 9:
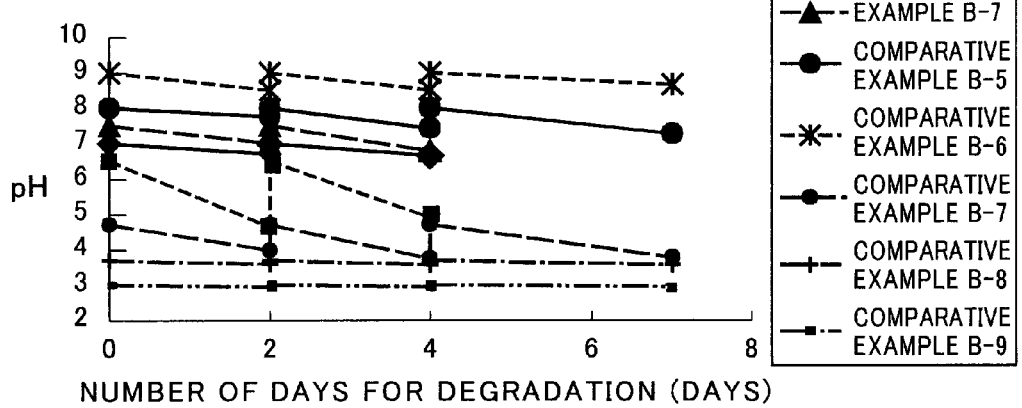
FIG. 9 shows change with time in pH in a case where a readily degradable resin composition was degraded in an enzyme solution of CLE.
Figure 10:
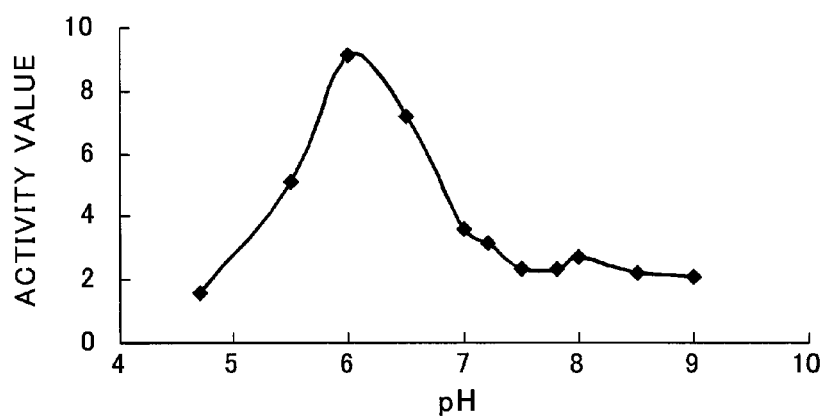
FIG. 10 shows degradation activity of pro K on polylactic acid film.
Figure 11:
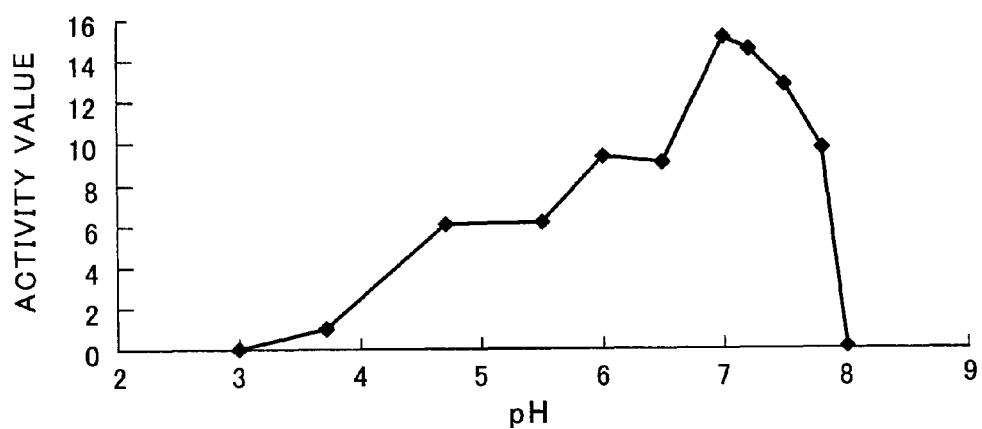
FIG. 11 shows degradation activity of CLE on polylactic acid film.

The invention claimed is:

1. A method for degrading a readily degradable resin composition comprising an aliphatic polyester (A) which is biodegradable, and an aliphatic polyester (B') which releases an acid upon hydrolysis and which is biodegradable at a higher degradation rate than that of the aliphatic polyester (A), the method comprising:
   (a) determining the maximum activity pH value at which the degradation activity value of a hydrolase, when used to degrade a simple polymer of the aliphatic polyester (A) alone in a buffer solution, is maximized;
   (b) determining an active pH range in which the degradation activity value is not less than 30% of the degradation activity value at the maximum activity pH value; and
   (c) degrading the readily degradable resin composition in an enzyme reaction liquid containing the hydrolase, and having a pH which is within the active pH range and which is less than 8.0, wherein the pH of the enzyme reaction liquid is maintained within the active pH range and at less than 8.0 in the degradation step.

2. The degradation method according to claim 1, wherein the degradation temperature is a temperature that is between the temperature that is 5° C. lower than the glass transition temperature of the aliphatic polyester (B') and the temperature that is the maximum temperature at which the enzyme is active.

3. The degradation method according to claim 1, wherein the hydrolase is a protease, lipase, cellulase, or cutinase.

4. The degradation method according to claim 1, wherein the acid released from the aliphatic polyester (B') is oxalic acid or maleic acid.

5. The degradation method according to claim 1, wherein the readily degradable resin composition is one which is obtained by dispersing a polyoxalate in a polylactic acid-based resin.

\* \* \* \* \*